US011174235B2

(12) United States Patent
Servesko et al.

(10) Patent No.: US 11,174,235 B2
(45) Date of Patent: Nov. 16, 2021

(54) CARBOXY ALKYL-ESTER ANTI-AGGLOMERANTS FOR THE CONTROL OF NATURAL GAS HYDRATES

(71) Applicant: ChampionX USA Inc., Sugar Land, TX (US)

(72) Inventors: Jeff Michael Servesko, Sugar Land, TX (US); Jeremy Wayne Bartels, Sugar Land, TX (US); Regan Andrew Jones, Sugar Land, TX (US); Corbin Metoyer, Pearland, TX (US)

(73) Assignee: ChampionX USA Inc., Sugar Land, TX (US)

( * ) Notice: Subject to any disclaimer, the term of this patent is extended or adjusted under 35 U.S.C. 154(b) by 0 days.

(21) Appl. No.: 16/440,663

(22) Filed: Jun. 13, 2019

(65) Prior Publication Data

US 2019/0382360 A1 Dec. 19, 2019

Related U.S. Application Data

(60) Provisional application No. 62/684,929, filed on Jun. 14, 2018.

(51) Int. Cl.

| C07D 295/15 | (2006.01) |
| C07C 229/24 | (2006.01) |
| C02F 1/68 | (2006.01) |
| C07C 67/12 | (2006.01) |
| C07C 227/10 | (2006.01) |
| C07C 231/12 | (2006.01) |
| C07C 233/20 | (2006.01) |
| C10G 75/04 | (2006.01) |
| C10L 3/10 | (2006.01) |
| C10L 10/04 | (2006.01) |

(52) U.S. Cl.
CPC .............. *C07D 295/15* (2013.01); *C02F 1/68* (2013.01); *C07C 67/12* (2013.01); *C07C 227/10* (2013.01); *C07C 229/24* (2013.01); *C07C 231/12* (2013.01); *C07C 233/20* (2013.01); *C10G 75/04* (2013.01); *C10L 3/107* (2013.01); *C10L 10/04* (2013.01); *C10G 2300/80* (2013.01); *C10L 2270/10* (2013.01); *C10L 2290/24* (2013.01)

(58) Field of Classification Search
CPC ........................... C07C 227/10; C07D 295/15
USPC ....................................................... 560/169
See application file for complete search history.

(56) References Cited

U.S. PATENT DOCUMENTS

| 4,326,069 A * | 4/1982 | Stockinger ............ C07D 231/12 |
| | | 546/232 |
| 4,501,852 A | 2/1985 | Markusch et al. |
| 5,736,604 A | 4/1998 | Luthra |
| 6,232,273 B1 | 5/2001 | Namba et al. |
| 6,566,309 B1 | 5/2003 | Klug et al. |
| 6,682,880 B2 * | 1/2004 | Kuse ........................ G03C 7/42 |
| | | 430/450 |
| 9,051,410 B2 | 6/2015 | Heckroth et al. |
| 9,375,509 B2 | 6/2016 | Heckroth et al. |
| 9,764,058 B2 | 9/2017 | Heckroth et al. |
| 2004/0164278 A1 | 8/2004 | Dahlmann et al. |
| 2013/0244918 A1 | 9/2013 | Barton et al. |
| 2016/0046855 A1 | 2/2016 | Mastrangelo et al. |
| 2016/0230077 A1 | 8/2016 | Mastrangelo et al. |
| 2017/0036992 A1 * | 2/2017 | Jandeleit ................. A61P 13/08 |
| 2017/0096610 A1 | 4/2017 | Bush et al. |
| 2017/0190947 A9 | 7/2017 | Acosta et al. |

FOREIGN PATENT DOCUMENTS

| CN | 103752210 A | 4/2014 | |
| GB | 2551945 A * | 1/2018 | ................ A61P 3/04 |
| JP | H06-321876 | 11/1994 | |
| WO | 2007/072983 A1 | 6/2007 | |
| WO | 2017096159 A1 | 6/2017 | |

OTHER PUBLICATIONS

Karten, Marvin J. et al., N-Substituted DL-aspartic acids and .beta.-methyl esters, Chemical Abstract XP002793885 (1966), Journal of Medicinal Chemistry, 1 page.

Cvikova, D., Proton NMR studies of acid-base properties and conformation of n-alkyl derivatives of asparic acid, Chemical Abstract XP002793886 (1982), 1 page.

Zender, Lars, Small interfering RNA and other inhibitors of mitogen-activated protein kinase 4 expression for liver regeneration and for treatment of liver failure, Chemical Abstract XP002793887 (2012), 5 pages.

Goldfarb, David Scott, Method using lifespan-altering compounds for altering the lifespan of eukaryotic organisms, and screening for such compounds, Chemical Abstract XP002793888 (2009), 2 pages.

Hirai, Atsushi, Higher fatty acid esters or amides having diethylenetriamine chelating sites, there chelates, liposomes containing them, and uses as the liposomes as imaging agents, Chemical Abstract XP002793889 (2007), 2 pages.

Bert, P. et al., Surfactants with ampholytic and chelating properties derived from aspartic acid, Chemical Abstract XP002793890 (1969), 1 page.

Laliberte, R. et al., Improved synthesis of N-alkylaspartic acids, Chemical Abstract XP002793891 (1962), 1 page.

(Continued)

*Primary Examiner* — Ana Z Muresan

(74) *Attorney, Agent, or Firm* — Stinson LLP

(57) ABSTRACT

This disclosure relates to anti-agglomerant low dosage hydrate inhibitors that can inhibit the formation of hydrate agglomerants and/or plugs. Thus, provided herein are carboxy alkyl ester compounds that can be used in hydrate inhibitor compositions and methods of inhibiting formation of hydrate agglomerants in a fluid comprising water, a gas, and optionally a liquid hydrocarbon. Also provided herein are methods of making the carboxy alkyl ester compound.

16 Claims, No Drawings

(56) References Cited

OTHER PUBLICATIONS

Lohse, Friedrich et al., N-Substituted derivatives of aspartic acid and epoxy resins produced with their aid, Chemical Abstract XP002793892 (1981), 2 pages.
Ota, Takashi et al., Composition of reclaimed polyester resin and its manufacture, Chemical Abstract XP002793893 (2003), 1 page.
International Search Report and Written Opinion dated Sep. 11, 2019 relating to PCT Application No. PCT/US2019/036920, 25 pages.

* cited by examiner

CARBOXY ALKYL-ESTER ANTI-AGGLOMERANTS FOR THE CONTROL OF NATURAL GAS HYDRATES

CROSS REFERENCE TO RELATED APPLICATIONS

This application claims priority to U.S. Provisional Patent Application Ser. No. 62/684,929 filed on Jun. 14, 2018, the disclosure of which is incorporated herein by reference in its entirety.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

REFERENCE TO A SEQUENCE LISTING, TABLE, OR COMPUTER PROGRAM LISTING APPENDIX SUBMITTED ON A COMPACT DISC AND AN INCORPORATION-BY-REFERENCE OF THE MATERIAL ON A COMPACT DISC

Not applicable.

FIELD OF THE INVENTION

Compounds, compositions and methods for reducing or inhibiting the growth, formation, and/or agglomeration of hydrate particles in fluids are provided. Also provided herein are methods of making the hydrate inhibitor compounds.

BACKGROUND OF THE INVENTION

Natural gas hydrates are crystalline solids composed of water and gas. In these solids, the gas molecules (guests) are trapped in water cavities (host) that are composed of hydrogen-bonded water molecules. Methane is the main gas in naturally occurring gas hydrates, however carbon dioxide, hydrogen sulfide, and less frequently, other hydrocarbons such as ethane and propane can be found within the hydrate structure. In 1934, Hammerschmidt determined that natural gas hydrates were blocking gas transmission lines, frequently at temperatures above the ice point. This discovery caused a more pragmatic interest in gas hydrates and led to the regulation of the water content in natural gas pipelines.

Gas hydrates can be easily formed during the transportation of oil and gas in pipelines under certain conditions. Factors affecting gas hydrate formation include gas composition, water content, temperature, and pressure, particularly low temperature and high pressure. While these crystalline cage-like structures are initially small, they are able to agglomerate into solid masses called gas hydrate plugs. The formation of gas hydrates with a pipeline often results in lost oil or gas production, damage to transmission lines and equipment, and safety hazard to field workers.

Three types of hydrate inhibitors are currently available to the energy industry for controlling gas hydrates: thermodynamic hydrate inhibitors (THIs), kinetic hydrate inhibitors (KHIs), and anti-agglomerants (AAs). The amount of chemical needed to prevent blockages varies widely depending upon the type of inhibitor employed. Thermodynamic hydrate inhibitors are substances that can reduce the temperature at which the hydrates form at a given pressure and water content, and are typically used at very high concentrations (regularly dosed as high as 50% based on water content—glycol is often used in amounts as high as 100% of the weight of the produced water). Therefore, there is a substantial cost associated with the transportation and storage of large quantities of these solvents. A more cost-effective alternative is the use of low dosage hydrate inhibitors (LDHIs), as they generally require a dose less than about 2% to inhibit the nucleation or growth of gas hydrates. There are two general types of LDHIs: kinetic hydrate inhibitors and anti-agglomerants, which are both typically used at much lower concentrations. KHIs work by delaying the growth of gas hydrate crystals. They also function as anti-nucleators. In contrast, AAs allow hydrates to form but are prevented from agglomerating and subsequently accumulating into larger masses capable of causing plugs. The function of an AA is to keep hydrate particles dispersed as a fluid slurry within the hydrocarbon phase.

Thus, there is an ongoing need for compounds and compositions having an anti-agglomerant effect and methods of administering the compounds and compositions to prevent gas hydrate agglomeration.

BRIEF SUMMARY OF THE INVENTION

Compounds, compositions, and methods relate to anti-agglomerant low dosage hydrate inhibitors that can inhibit the formation of hydrate agglomerants and/or plugs are described herein. In this respect, a hydrate inhibitor compound of formula (1) is disclosed:

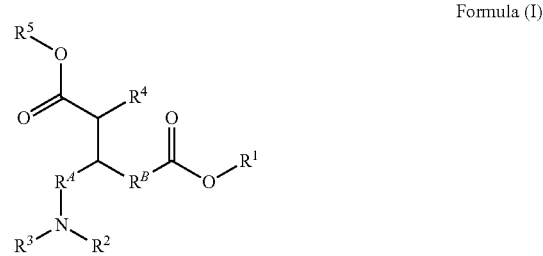

Formula (I)

wherein $R^A$ and $R^B$ are independently a bond or a $C_1$-$C_4$ alkylene group; $R^1$ and $R^5$ are independently hydrogen, alkyl, alkenyl, alkynyl, cycloalkyl, aryl, or alkylaryl wherein each group can optionally be substituted with an amine, an ester, an alkoxy, a hydroxyl, a halo, or a carboxyl group, and wherein each alkyl, alkenyl, alkynyl, cycloalkyl, or alkylaryl group can optionally have one or more —$CH_2$— groups replaced with an amine, a carbonyl, an ether, an amide, or an ester group; $R^2$ and $R^3$ are independently hydrogen, alkyl, alkenyl, or alkynyl, wherein each group can optionally be substituted with an amine, a hydroxyl, or a carboxyl, and wherein each alkyl, alkenyl, or alkynyl group can optionally have one or more —$CH_2$— groups replaced with an amine, a carbonyl, an ether, an amide, or an ester group, or $R^2$ and $R^3$ together with the nitrogen they are attached to form a ring; $R^4$ is hydrogen or alkyl; provided that at least one of $R^1$ and $R^5$ is hydrogen when the other is other than hydrogen, and when $R^2$ and $R^3$ together with the nitrogen they are attached to do not form a ring, at least one of $R^1$, $R^2$, $R^3$, and $R^5$ is a straight or branched alkyl or alkenyl group, wherein at least one of the —$CH_2$— groups is replaced by an amine.

The compound of formula (I), can have $R^A$ and $R^B$ independently be a bond, a methylene group, or an ethylene group; preferably, $R^A$ and $R^B$ can be a bond.

The compound of formula (I) can have at least one of $R^1$, $R^2$, $R^3$, and $R^5$ be a straight or branched alkyl group, wherein at least one of the —$CH_2$— groups is replaced by an amine group.

The compound of formula (I) can have $R^1$ be alkyl, alkenyl, cycloalkyl, aryl, or alkylaryl wherein each group can optionally be substituted with an amine, a hydroxyl, or a carboxyl group, and wherein each alkyl, alkenyl, cycloalkyl, or alkylaryl group can optionally have one or more —$CH_2$— groups replaced with an amine, a carbonyl, or an ether and $R^5$ can be hydrogen; or $R^5$ can be alkyl, alkenyl, cycloalkyl, aryl, or alkylaryl wherein each group can optionally be substituted with an amine, a hydroxyl, or a carboxyl group, and wherein each alkyl, alkenyl, cycloalkyl, or alkylaryl group can optionally have one or more —$CH_2$— groups replaced with an amine, a carbonyl, or an ether; and $R^1$ can be hydrogen.

The compound of formula (I) can have $R^1$ be alkyl, or alkenyl wherein each group can optionally be substituted with an amine, a hydroxyl, or a carboxyl group, and wherein each alkyl, or alkenyl group can optionally have one or more —$CH_2$— groups replaced with an amine or an ether; and $R^5$ be hydrogen; or $R^5$ be alkyl, or alkenyl wherein each group can optionally be substituted with an amine, a hydroxyl, or a carboxyl group, and wherein each alkyl, or alkenyl group can optionally have one or more —$CH_2$— groups replaced with an amine or an ether; and $R^1$ be hydrogen.

The compound of formula (I) can have $R^1$ be straight or branched $C_6$-$C_{24}$ alkyl and contains 1 to 12 ethylene oxide units; and $R^5$ be hydrogen; or $R^5$ can be straight or branched $C_6$-$C_{24}$ alkyl and contains 1 to 12 ethylene oxide units; and $R^1$ can be hydrogen.

Additionally, the compounds of formula (I) described herein can have $R^2$ and $R^3$ independently be hydrogen, alkyl, or alkenyl, wherein each group can optionally be substituted with an amine, a hydroxyl, or a carboxyl, and wherein each group can optionally have one or more —$CH_2$— groups replaced with an amine, a carbonyl, or an ether group, or $R^2$ and $R^3$ together with the nitrogen they are attached to form a ring.

In the compounds of formula (I) described herein, preferably, $R^2$ is hydrogen or a straight or branched alkyl group, and $R^3$ is a straight or branched alkyl group wherein one of the —$CH_2$— groups is replaced by an amine group.

The compounds of formula (I) can have $R^4$ be hydrogen.

In various preferred compounds of formula (I), $R^1$ can be a straight or branched alkyl group, $R^2$ can be hydrogen or a straight or branched alkyl group, $R^3$ can be a straight or branched alkyl group wherein one of the alkylene groups is replaced by an amine group, and $R^5$ can be hydrogen.

Compounds of formula (I) can have $R^1$ be a straight or branched alkenyl group, $R^2$ be hydrogen or a straight or branched alkyl group, and $R^3$ be a straight or branched alkyl group wherein one of the alkylene groups is replaced by an amine group, and $R^5$ be hydrogen.

The compounds of formula (I) can have the structure of formula (Ia) or an acid, a free base, a zwitterion, or a salt thereof:

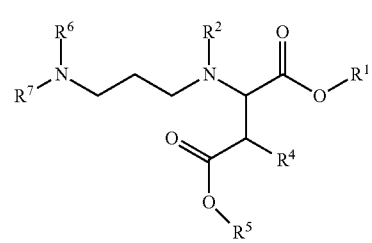

Formula (Ia)

wherein $R^1$ and $R^5$ are independently hydrogen, alkyl, alkenyl, alkynyl, cycloalkyl, aryl, or alkylaryl, wherein each group can optionally be substituted with an amine, a hydroxyl, or a carboxyl, and wherein each alkyl, alkenyl, or alkynyl group can optionally have one or more —$CH_2$— groups replaced with an amine, a carbonyl, an ether, an amide, or an ester group; $R^2$ is hydrogen, alkyl, alkenyl, or alkynyl, wherein each group can optionally be substituted with an amine, a hydroxyl, or a carboxyl, and wherein each alkyl, alkenyl, or alkynyl group can optionally have one or more —$CH_2$— groups replaced with an amine, a carbonyl, an ether, an amide, or an ester group; $R^4$ is hydrogen or alkyl; and $R^6$ and $R^7$ are independently hydrogen, alkyl, alkenyl, or alkynyl, wherein each group can optionally be substituted with an amine, a hydroxyl, or a carboxyl, and wherein each alkyl, alkenyl, or alkynyl group can optionally have one or more —$CH_2$— groups replaced with an amine, a carbonyl, an ether, an amide, or an ester group, or $R^6$ and $R^7$ together with the nitrogen they are attached to form a ring; provided that at least one of $R^1$ and $R^5$ is hydrogen when the other is other than hydrogen, and at least one of $R^2$, $R^6$, and $R^7$ is other than hydrogen.

For the compounds of formula (I), $R^2$ can be carboxyl-substituted alkyl.

Also, the compounds of formula (I) can have the structure of formula (Ib) or an acid, a free base, a zwitterion, or a salt thereof:

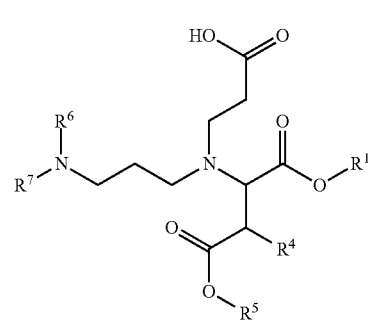

Formula (Ib)

wherein $R^1$ and $R^5$ are independently hydrogen, alkyl, or alkenyl, wherein each group can optionally be substituted with an amine, a hydroxyl, or a carboxyl, and wherein each alkyl, or alkenyl group can optionally have one or more —$CH_2$— groups replaced with an amine, a carbonyl, or an ether group; $R^4$ is hydrogen or alkyl; and $R^6$ and $R^7$ are independently hydrogen, alkyl, or alkenyl, wherein each alkyl, or alkenyl group can optionally have one or more —$CH_2$— groups replaced with an amine, a carbonyl, or an ether group, or $R^6$ and $R^7$ together with the nitrogen they are attached to form a ring; provided that at least one of $R^1$ and $R^5$ is hydrogen when the other is other than hydrogen.

The compound of formula (I) can also have the structure of formula (Ic) or an acid, a free base, a zwitterion, or a salt thereof:

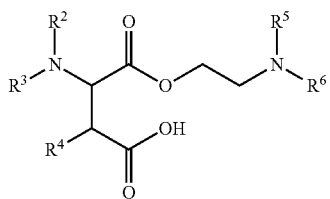

Formula (Ic)

wherein $R^2$ and $R^3$ are independently hydrogen, alkyl, alkenyl, or alkynyl, wherein each alkyl, alkenyl, or alkynyl group can optionally be substituted with an amine, a hydroxyl, or a carboxyl, and wherein each alkyl, alkenyl, or alkynyl group can optionally have one or more —$CH_2$— groups replaced with an amine, a carbonyl, or an ether group, or $R^2$ and $R^3$ together with the nitrogen they are attached to form a ring; $R^4$ is hydrogen or alkyl; and $R^5$ and $R^6$ are independently hydrogen, alkyl, alkenyl, alkynyl, cycloalkyl, aryl, or alkylaryl, wherein each group can optionally be substituted with an amine, a hydroxyl, or a carboxyl, and wherein each alkyl, alkenyl, or alkynyl group can optionally have one or more —$CH_2$— groups replaced with an amine, a carbonyl, an ether, an amide, or an ester group, or $R^5$ and $R^6$ together with the nitrogen they are attached to form a ring; wherein at least one of $R^2$, $R^3$, $R^5$, and $R^6$ is other than hydrogen.

The compounds of formula (Ic) can have $R^2$ be carboxyl-substituted alkyl.

The compounds of formula (I) can also have the structure of formula (Id) or an acid, a free base, a zwitterion, or a salt thereof:

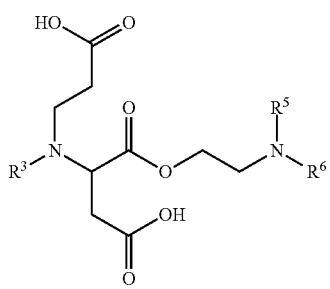

Formula (Id)

wherein $R^3$ is independently hydrogen, alkyl, alkenyl, or alkynyl, wherein each alkyl, alkenyl, or alkynyl group can optionally be substituted with an amine, a hydroxyl, or a carboxyl, and wherein each alkyl, alkenyl, or alkynyl group can optionally have one or more —$CH_2$— groups replaced with an amine, a carbonyl, or an ether group; and $R^5$ and $R^6$ are independently hydrogen, alkyl, alkenyl, alkynyl, cycloalkyl, aryl, or alkylaryl, wherein each group can optionally be substituted with an amine, a hydroxyl, or a carboxyl, and wherein each alkyl, alkenyl, or alkynyl group can optionally have one or more —$CH_2$— groups replaced with an amine, a carbonyl, or an ether group, or $R^5$ and $R^6$ together with the nitrogen they are attached to form a ring.

The compounds of formula (I) can also have the structure of formula (Ie) or an acid, a free base, a zwitterion, or a salt thereof:

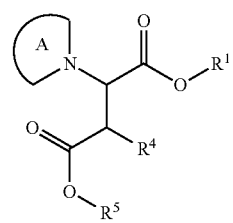

Formula (Ie)

wherein $R^1$ and $R^5$ are independently hydrogen, alkyl, or alkenyl, wherein each group can optionally be substituted with an amine, a hydroxyl, or a carboxyl, and wherein each alkyl, or alkenyl group can optionally have one or more —$CH_2$— groups replaced with an amine, a carbonyl, or an ether group; $R^4$ is hydrogen or alkyl; A is a nitrogen-containing heterocycle; provided that at least one of $R^1$ and $R^5$ is hydrogen when the other is other than hydrogen.

The compounds of Formula (Ie) can have $R^1$ be hydrogen.

The compounds of Formula (Ie) can have can have $R^4$ be hydrogen.

The compounds of Formula (Ie) can have $R^5$ be alkyl or alkenyl, wherein each group can optionally have one or more —$CH_2$— groups replaced with an amine or an ether group.

The compounds of Formula (Ie) can have $R^5$ be unsubstituted alkyl or alkenyl.

The compounds of Formula (Ie) can have $R^5$ be alkyl having one or more —$CH_2$— groups replaced with an amine or an ether group.

The compounds of Formula (Ie) can have $R^5$ be alkyl having one or more —$CH_2$— groups replaced with an ether group.

The compounds of formulae (Ia) and (Ib) can have $R^6$ and $R^7$ independently be hydrogen, $C_1$-$C_{10}$ alkyl, $C_1$-$C_{10}$ alkenyl, or $C_1$-$C_{10}$ alkynyl. Preferably, for the compounds of formulae (Ia) and (Ib), $R^6$ and $R^7$ are the same.

The compounds of formulae (Ic) and (Id) can have $R^5$ and $R^6$ independently be hydrogen, $C_1$-$C_{10}$ alkyl, $C_1$-$C_{10}$ alkenyl, or $C_1$-$C_{10}$ alkynyl. Preferably, for the compounds of formulae (Ic) and (Id), $R^5$ and $R^6$ are the same.

The compounds of formulae (Ic) and (Id) can have $R^3$ be $C_6$-$C_{24}$ alkyl, $C_6$-$C_{24}$ alkenyl, or $C_6$-$C_{24}$ alkynyl.

The compounds of formula (I) can be selected from the group consisting of:

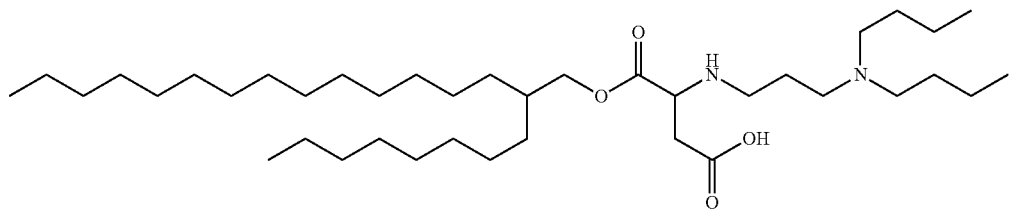

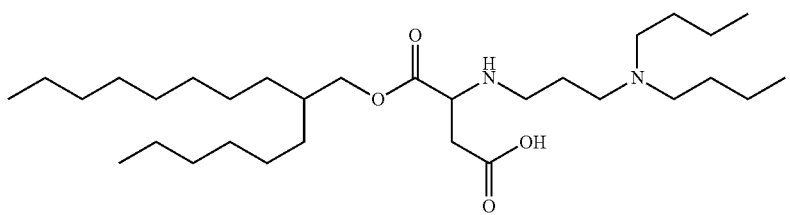
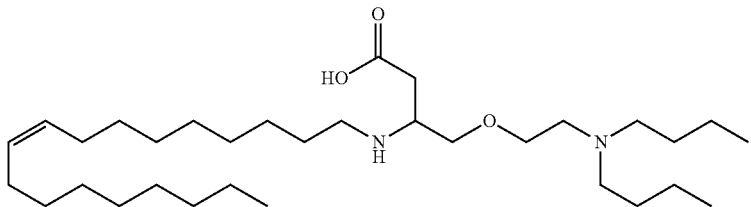
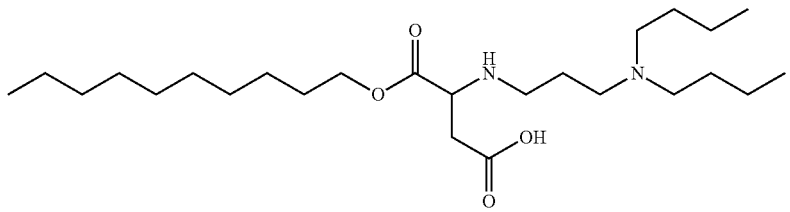
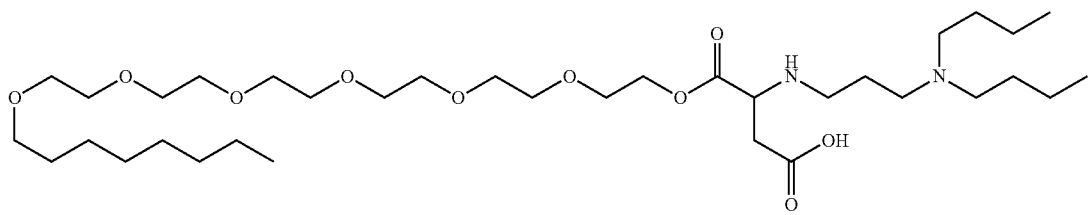
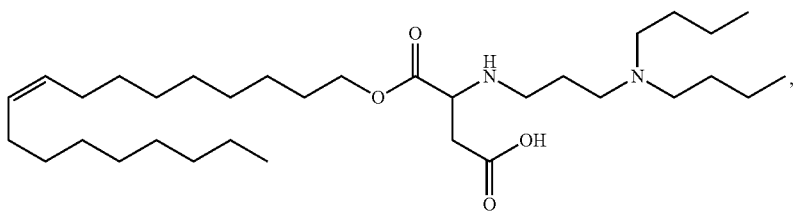
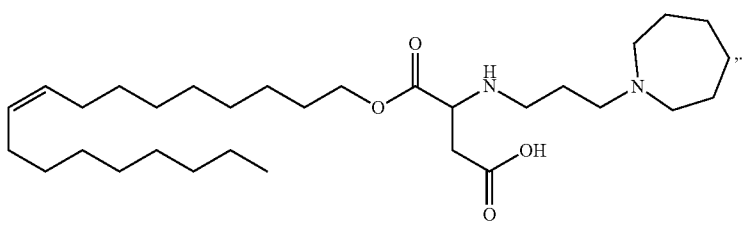
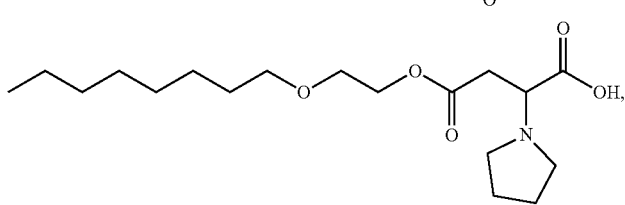
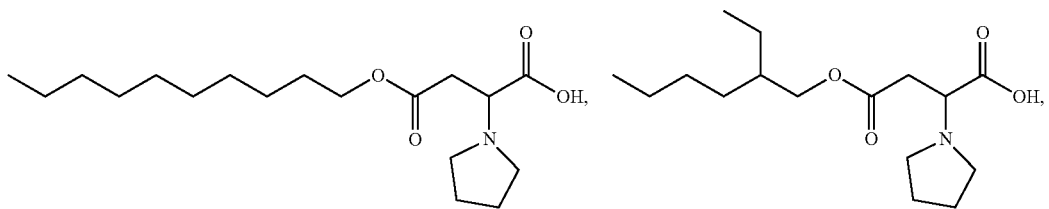

-continued

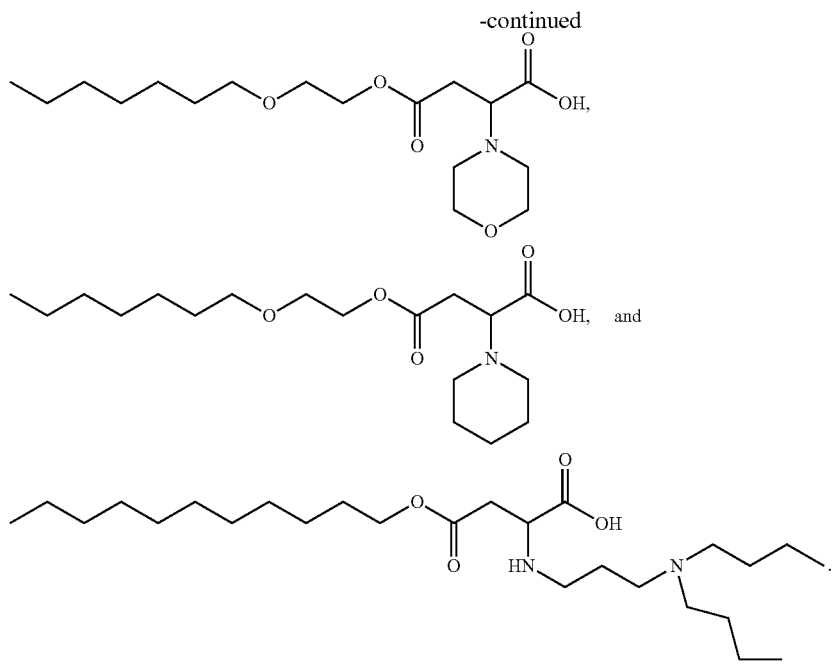

The compounds of formula (I) can be prepared by the following method of synthesis:

Formula (I)

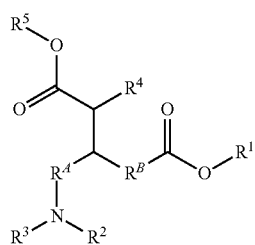

the method comprising contacting an alcohol corresponding in structure to formula (II):

 R$^1$—OH      Formula (II)

or

 R$^5$—OH      Formula (II')

with an acid anhydride of formula (III) to produce an intermediate:

Formula (III)

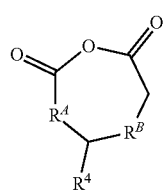

and contacting the intermediate with an amine corresponding in structure to formula (IV):

Formula (IV)

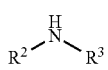

to produce a compound corresponding in structure to formula (I), wherein R$^A$ is a bond or a C$_1$-C$_4$ alkylene group; R$^B$ is a bond, a double bond, or a C$_1$-C$_4$ alkylene group; R$^1$ and R$^5$ are independently hydrogen, alkyl, alkenyl, alkynyl, cycloalkyl, aryl, or alkylaryl, wherein each group can optionally be substituted with an amine, a hydroxyl, or a carboxyl, and wherein each alkyl, alkenyl, alkynyl, cycloalkyl, or alkylaryl group can optionally have one or more —CH$_2$— groups replaced with an amine, a carbonyl, an ether, an amide, or an ester group; R$^2$ and R$^3$ are independently hydrogen, alkyl, alkenyl, or alkynyl, wherein each alkyl, alkenyl, or alkynyl group can optionally be substituted with an amine, a hydroxyl, or a carboxyl, and wherein each alkyl, alkenyl, or alkynyl group can optionally have one or more —CH$_2$— groups replaced with an amine, a carbonyl, an ether, an amide, or an ester group; or R$^2$ and R$^3$ together with the nitrogen they are attached to form a ring; and R$^4$ is hydrogen, alkyl, alkenyl, or alkynyl; provided that at least one of R$^1$ and R$^5$ is hydrogen when the other is other than hydrogen and at least one of R$^1$, R$^2$, R$^3$, and R$^5$ is a straight or branched alkyl group, wherein when R$^2$ and R$^3$ together with the nitrogen they are attached to do not form a ring, at least one of R$^1$, R$^2$, R$^3$, and R$^5$ is a straight or branched alkyl or alkenyl group, wherein at least one of the —CH$_2$— groups is replaced by an amine or an ether group.

The method of synthesis described herein can have the acid anhydride of formula (III) comprise maleic anhydride, itaconic anhydride, citraconic anhydride, glutaconic anhydride, or a combination thereof.

The method of synthesis can further have the amine of formula (IV) comprise aminopropyl pyrrolidine, aminopropyl azepane, dibutylaminopropylamine (DBAPA), or a combination thereof.

The method of synthesis can also have the alcohol of formula (II) comprise 2-ethylhexanol, pentanol, hexanol, heptanol, octanol, decanol, dodecanol, isostearyl alcohol, 2-decyltetradecanol, 11-methyldodecanol, or a combination thereof.

The method of synthesis can have $R^1$ be straight or branched $C_6$-$C_{24}$ alkyl or $C_6$-$C_{24}$ alkenyl. Additionally, for the method of synthesis, $R^1$ can comprise 1 to 12 ethylene oxide units.

The method of synthesis described herein can have the compound of formula (I) be contacted with an organic acid to provide a salt of formula (I). Preferably, the organic acid comprises acetic acid, acrylic acid, or a combination thereof.

The compounds can also have a structure corresponding to formula (V):

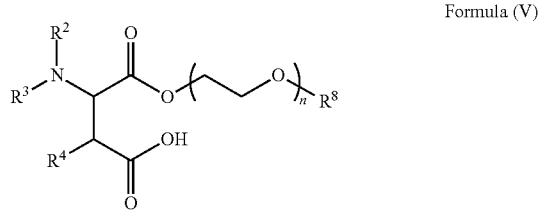

Formula (V)

wherein $R^2$ and $R^3$ are independently alkyl, alkenyl, or alkynyl, wherein each alkyl, alkenyl, or alkynyl group can optionally be substituted with an amine, a hydroxyl, or a carboxyl, and wherein each alkyl, alkenyl, or alkynyl group can optionally have one or more —$CH_2$— groups replaced with an amine, a carbonyl, or an ether group; $R^4$ is hydrogen or alkyl; and $R^8$ is alkyl or alkenyl, wherein each group can optionally be substituted with an amine, a hydroxyl, or a carboxyl, and wherein each alkyl or alkenyl group can optionally have one or more —$CH_2$— groups replaced with an amine, a carbonyl, an ether, an amide, or an ester group; and n is an integer from 0 to 10.

The compounds of formula (I) can also be present in a hydrate inhibitor composition comprising a hydrate-inhibiting effective amount of a compound of formula (I), as described above, and methods of inhibiting formation of hydrate agglomerants in a fluid comprising water, a gas, and optionally a liquid hydrocarbon, the method comprising contacting the fluid with an effective amount of a hydrate inhibitor composition.

The hydrate inhibitor composition described herein can further comprise a thermodynamic hydrate inhibitor, a kinetic hydrate inhibitor, an anti-agglomerant, or a combination thereof.

The hydrate inhibitor composition described herein can further comprise a polar solvent, a non-polar solvent, or a combination thereof.

The hydrate inhibitor composition described herein can also further comprise an organic solvent, a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof.

The hydrate inhibitor compositions and compounds of formula (I) can also be used in a method of inhibiting formation of hydrate agglomerants in a fluid comprising water, a gas, and optionally a liquid hydrocarbon, the method comprising contacting the fluid with an effective amount of a hydrate inhibitor composition or compound of formula (I) described herein.

The method of inhibiting formation of hydrate agglomerants can use an effective amount of the hydrate inhibitor composition of from about 0.1 to about 10 vol % based on the amount of water.

The method of inhibiting formation of hydrate agglomerants can be used for fluids contained in an oil or gas pipeline or oil or gas refinery.

For some of the method of inhibiting formation of hydrate agglomerants, the composition is added downhole near a surface controlled sub-sea safety valve.

The method of inhibiting formation of hydrate agglomerants can have the water comprise a salinity of about 0% to about 25% weight/weight total dissolved solids (TDS).

Other objects and features will be in part apparent and in part pointed out hereinafter.

DETAILED DESCRIPTION OF THE INVENTION

The disclosure is directed to anti-agglomerant low dosage hydrate inhibitors that can inhibit the formation of hydrate agglomerants and/or plugs. Hereinafter, these compounds (anti-agglomerant low dosage hydrate inhibitors) may simply be referred to as "hydrate inhibitors."

The hydrate inhibitors may be used for inhibiting, retarding, mitigating, reducing, controlling and/or delaying formation of hydrocarbon hydrates, agglomerants of hydrates, and/or plugs. For example, the hydrate inhibitors may be applied to prevent, reduce and/or mitigate plugging of conduits, pipes, transfer lines, valves, and other places or equipment where hydrocarbon hydrate solids may form.

Compounds, compositions, and methods relate to anti-agglomerant low dosage hydrate inhibitors that can inhibit the formation of hydrate agglomerants and/or plugs are described herein. In this respect, a hydrate inhibitor compound of formula (1) is disclosed:

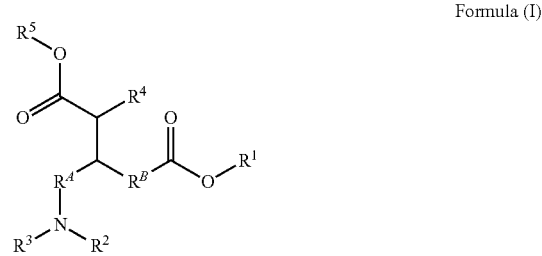

Formula (I)

wherein $R^A$ and $R^B$ are independently a bond or a $C_1$-$C_4$ alkylene group; $R^1$ and $R^5$ are independently hydrogen, alkyl, alkenyl, alkynyl, cycloalkyl, aryl, or alkylaryl wherein each group can optionally be substituted with an amine, an ester, an alkoxy, a hydroxyl, a halo, or a carboxyl group, and wherein each alkyl, alkenyl, alkynyl, cycloalkyl, or alkylaryl group can optionally have one or more —$CH_2$— groups replaced with an amine, a carbonyl, an ether, an amide, or an ester group; $R^2$ and $R^3$ are independently hydrogen, alkyl, alkenyl, or alkynyl, wherein each group can optionally be substituted with an amine, a hydroxyl, or a carboxyl, and wherein each alkyl, alkenyl, or alkynyl group can optionally have one or more —$CH_2$— groups replaced with an amine, a carbonyl, an ether, an amide, or an ester group, or $R^2$ and $R^3$ together with the nitrogen they are attached to form a ring; $R^4$ is hydrogen or alkyl; provided that at least one of $R^1$ and $R^5$ is hydrogen when the other is other than hydrogen, and when $R^2$ and $R^3$ together with the nitrogen they are attached to do not form a ring, at least one of $R^1$, $R^2$, $R^3$, and $R^5$ is a straight or branched alkyl or alkenyl group, wherein at least one of the —$CH_2$— groups is replaced by an amine.

The compound of formula (I), can have $R^A$ and $R^B$ independently be a bond, a methylene group, or an ethylene group; preferably, $R^A$ and $R^B$ can be a bond.

The compound of formula (I) can have at least one of $R^1$, $R^2$, $R^3$, and $R^5$ be a straight or branched alkyl group, wherein at least one of the —$CH_2$— groups is replaced by an amine group.

The compound of formula (I) can have $R^1$ be alkyl, alkenyl, cycloalkyl, aryl, or alkylaryl wherein each group can optionally be substituted with an amine, a hydroxyl, or a carboxyl group, and wherein each alkyl, alkenyl, cycloalkyl, or alkylaryl group can optionally have one or more —$CH_2$— groups replaced with an amine, a carbonyl, or an ether and $R^5$ can be hydrogen; or $R^5$ can be alkyl, alkenyl, cycloalkyl, aryl, or alkylaryl wherein each group can optionally be substituted with an amine, a hydroxyl, or a carboxyl group, and wherein each alkyl, alkenyl, cycloalkyl, or alkylaryl group can optionally have one or more —$CH_2$— groups replaced with an amine, a carbonyl, or an ether; and $R^1$ can be hydrogen.

The compound of formula (I) can have $R^1$ be alkyl, or alkenyl wherein each group can optionally be substituted with an amine, a hydroxyl, or a carboxyl group, and wherein each alkyl, or alkenyl group can optionally have one or more —$CH_2$— groups replaced with an amine or an ether; and $R^5$ be hydrogen; or $R^5$ be alkyl, or alkenyl wherein each group can optionally be substituted with an amine, a hydroxyl, or a carboxyl group, and wherein each alkyl, or alkenyl group can optionally have one or more —$CH_2$— groups replaced with an amine or an ether; and $R^1$ be hydrogen.

The compound of formula (I) can have $R^1$ be straight or branched $C_6$-$C_{24}$ alkyl and contains 1 to 12 ethylene oxide units; and $R^5$ be hydrogen; or $R^5$ can be straight or branched $C_6$-$C_{24}$ alkyl and contains 1 to 12 ethylene oxide units; and $R^1$ can be hydrogen.

Additionally, the compounds of formula (I) described herein can have $R^2$ and $R^3$ independently be hydrogen, alkyl, or alkenyl, wherein each group can optionally be substituted with an amine, a hydroxyl, or a carboxyl, and wherein each group can optionally have one or more —$CH_2$— groups replaced with an amine, a carbonyl, or an ether group, or $R^2$ and $R^3$ together with the nitrogen they are attached to form a ring.

In the compounds of formula (I) described herein, preferably, $R^2$ is hydrogen or a straight or branched alkyl group, and $R^3$ is a straight or branched alkyl group wherein one of the —$CH_2$— groups is replaced by an amine group.

The compounds of formula (I) can have $R^4$ be hydrogen.

In various preferred compounds of formula (I), $R^1$ can be a straight or branched alkyl group, $R^2$ can be hydrogen or a straight or branched alkyl group, $R^3$ can be a straight or branched alkyl group wherein one of the alkylene groups is replaced by an amine group, and $R^5$ can be hydrogen.

Compounds of formula (I) can have $R^1$ be a straight or branched alkenyl group, $R^2$ be hydrogen or a straight or branched alkyl group, and $R^3$ be a straight or branched alkyl group wherein one of the alkylene groups is replaced by an amine group, and $R^5$ be hydrogen.

The compounds of formula (I) can have the structure of formula (Ia) or an acid, a free base, a zwitterion, or a salt thereof:

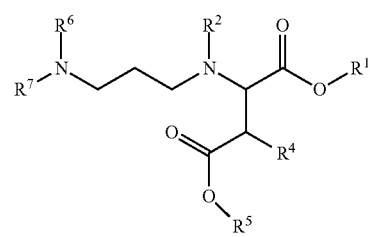

Formula (Ia)

wherein $R^1$ and $R^5$ are independently hydrogen, alkyl, alkenyl, alkynyl, cycloalkyl, aryl, or alkylaryl, wherein each group can optionally be substituted with an amine, a hydroxyl, or a carboxyl, and wherein each alkyl, alkenyl, or alkynyl group can optionally have one or more —$CH_2$— groups replaced with an amine, a carbonyl, an ether, an amide, or an ester group; $R^2$ is hydrogen, alkyl, alkenyl, or alkynyl, wherein each group can optionally be substituted with an amine, a hydroxyl, or a carboxyl, and wherein each alkyl, alkenyl, or alkynyl group can optionally have one or more —$CH_2$— groups replaced with an amine, a carbonyl, an ether, an amide, or an ester group; $R^4$ is hydrogen or alkyl; and $R^6$ and $R^7$ are independently hydrogen, alkyl, alkenyl, or alkynyl, wherein each group can optionally be substituted with an amine, a hydroxyl, or a carboxyl, and wherein each alkyl, alkenyl, or alkynyl group can optionally have one or more —$CH_2$— groups replaced with an amine, a carbonyl, an ether, an amide, or an ester group, or $R^6$ and $R^7$ together with the nitrogen they are attached to form a ring; provided that at least one of $R^1$ and $R^5$ is hydrogen when the other is other than hydrogen, and at least one of $R^2$, $R^6$, and $R^7$ is other than hydrogen.

For the compounds of formula (Ia) can have $R^1$ be $C_{10}$ to $C_{24}$ alkyl or alkenyl.

The compounds of formula (Ia) can also have $R^5$ be hydrogen.

Further, the compounds of formula (Ia) can have $R^2$ and $R^4$ be hydrogen.

The compounds of formula (Ia) can have $R^6$ and $R^7$ be $C_1$ to $C_6$ alkyl.

Preferably, the compounds of formula (Ia) can have $R^1$ be $C_{10}$ to $C_{24}$ alkyl or alkenyl, $R^2$, $R^4$, and $R^5$ be hydrogen, and $R^6$ and $R^7$ be $C_1$ to $C_6$ alkyl.

For the compounds of formula (I), $R^2$ can be carboxyl-substituted alkyl.

Also, the compounds of formula (I) can have the structure of formula (Ib) or an acid, a free base, a zwitterion, or a salt thereof:

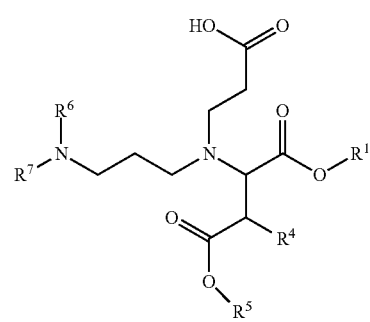

Formula (Ib)

wherein $R^1$ and $R^5$ are independently hydrogen, alkyl, or alkenyl, wherein each group can optionally be substituted with an amine, a hydroxyl, or a carboxyl, and wherein each alkyl, or alkenyl group can optionally have one or more —$CH_2$— groups replaced with an amine, a carbonyl, or an ether group; $R^4$ is hydrogen or alkyl; and $R^6$ and $R^7$ are independently hydrogen, alkyl, or alkenyl, wherein each alkyl, or alkenyl group can optionally have one or more —$CH_2$— groups replaced with an amine, a carbonyl, or an ether group, or $R^6$ and $R^7$ together with the nitrogen they are attached to form a ring; provided that at least one of $R^1$ and $R^5$ is hydrogen when the other is other than hydrogen.

The compound of formula (I) can also have the structure of formula (Ic) or an acid, a free base, a zwitterion, or a salt thereof:

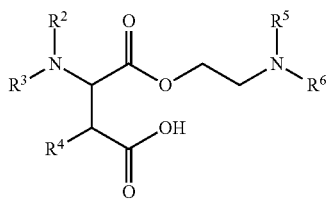

Formula (Ic)

wherein $R^2$ and $R^3$ are independently hydrogen, alkyl, alkenyl, or alkynyl, wherein each alkyl, alkenyl, or alkynyl group can optionally be substituted with an amine, a hydroxyl, or a carboxyl, and wherein each alkyl, alkenyl, or alkynyl group can optionally have one or more —$CH_2$— groups replaced with an amine, a carbonyl, or an ether group, or $R^2$ and $R^3$ together with the nitrogen they are attached to form a ring; $R^4$ is hydrogen or alkyl; and $R^5$ and $R^6$ are independently hydrogen, alkyl, alkenyl, alkynyl, cycloalkyl, aryl, or alkylaryl, wherein each group can optionally be substituted with an amine, a hydroxyl, or a carboxyl, and wherein each alkyl, alkenyl, or alkynyl group can optionally have one or more —$CH_2$— groups replaced with an amine, a carbonyl, an ether, an amide, or an ester group, or $R^5$ and $R^6$ together with the nitrogen they are attached to form a ring; wherein at least one of $R^2$, $R^3$, $R^5$, and $R^6$ is other than hydrogen.

The compounds of formula (Ic) can have $R^2$ be carboxyl-substituted alkyl.

The compounds of formula (I) can also have the structure of formula (Id) or an acid, a free base, a zwitterion, or a salt thereof:

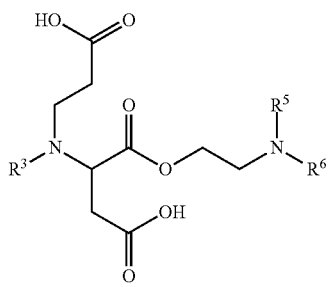

Formula (Id)

wherein $R^3$ is independently hydrogen, alkyl, alkenyl, or alkynyl, wherein each alkyl, alkenyl, or alkynyl group can optionally be substituted with an amine, a hydroxyl, or a carboxyl, and wherein each alkyl, alkenyl, or alkynyl group can optionally have one or more —$CH_2$— groups replaced with an amine, a carbonyl, or an ether group; and $R^5$ and $R^6$ are independently hydrogen, alkyl, alkenyl, alkynyl, cycloalkyl, aryl, or alkylaryl, wherein each group can optionally be substituted with an amine, a hydroxyl, or a carboxyl, and wherein each alkyl, alkenyl, or alkynyl group can optionally have one or more —$CH_2$— groups replaced with an amine, a carbonyl, or an ether group, or $R^5$ and $R^6$ together with the nitrogen they are attached to form a ring.

The compounds of formula (I) can also have the structure of formula (Ie) or an acid, a free base, a zwitterion, or a salt thereof:

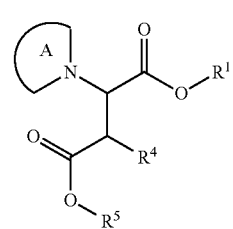

Formula (Ie)

wherein $R^1$ and $R^5$ are independently hydrogen, alkyl, or alkenyl, wherein each group can optionally be substituted with an amine, a hydroxyl, or a carboxyl, and wherein each alkyl, or alkenyl group can optionally have one or more —$CH_2$— groups replaced with an amine, a carbonyl, or an ether group; $R^4$ is hydrogen or alkyl; A is a nitrogen-containing heterocycle; provided that at least one of $R^1$ and $R^5$ is hydrogen when the other is other than hydrogen.

The nitrogen-containing heterocycle can be an optionally substituted pyrrole, pyrroline, pyrrolidine, piperidine, pyrazole, pyrazoline, pyrazolidine, imidazole, imidazoline, imidazolidine, triazole, isoxazole, isoxazoline, isoxazolidine, oxazole, oxazoline, oxazolidine, thiazole, isothiazole, oxadiazole, oxatriazole, dioxazole, oxathiazole, pyridine, pyridazine, pyrimidine, pyrazine, triazine, oxazine, oxathiazine, oxazine, isoxazine, oxadiazine, morpholine, azepane, azepine, caprolactam, or quinolone. Preferably, the nitrogen-containing heterocycle is an optionally substituted pyrrolidine, piperidine, pyrazolidine, imidazolidine, isoxazolidine, oxazolidine, or azepane. More preferably, the nitrogen-containing heterocycle is pyrrolidine.

The compounds of Formula (Ie) can have $R^1$ be hydrogen.
The compounds of Formula (Ie) can have can have $R^4$ be hydrogen.
The compounds of Formula (Ie) can have $R^5$ be alkyl or alkenyl, wherein each group can optionally have one or more —$CH_2$— groups replaced with an amine or an ether group.
The compounds of Formula (Ie) can have $R^5$ be unsubstituted alkyl or alkenyl.
The compounds of Formula (Ie) can have $R^5$ be alkyl having one or more —$CH_2$— groups replaced with an amine or an ether group.
The compounds of Formula (Ie) can have $R^5$ be alkyl having one or more —$CH_2$— groups replaced with an ether group.
The compounds of formulae (Ia) and (Ib) can have $R^6$ and $R^7$ independently be hydrogen, $C_1$-$C_{10}$ alkyl, $C_1$-$C_{10}$ alkenyl, or $C_1$-$C_{10}$ alkynyl. Preferably, for the compounds of formulae (Ia) and (Ib), $R^6$ and $R^7$ are the same.

The compounds of formulae (Ic) and (Id) can have $R^5$ and $R^6$ independently be hydrogen, $C_1$-$C_{10}$ alkyl, $C_1$-$C_{10}$ alkenyl, or $C_1$-$C_{10}$ alkynyl. Preferably, for the compounds of formulae (Ic) and (Id), $R^5$ and $R^6$ are the same.

The compounds of formulae (Ic) and (Id) can have $R^3$ be $C_6$-$C_{24}$ alkyl, $C_6$-$C_{24}$ alkenyl, or $C_6$-$C_{24}$ alkynyl.

The compounds of formula (I) can be selected from the group consisting of:

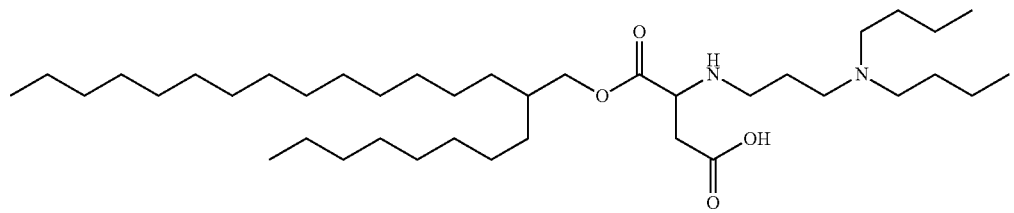

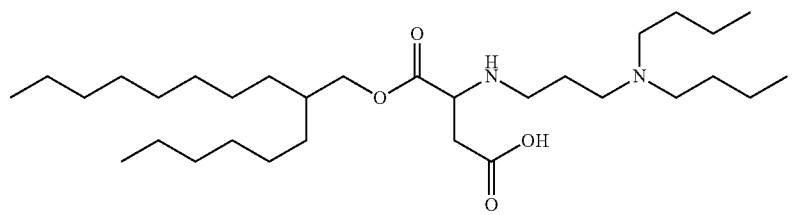

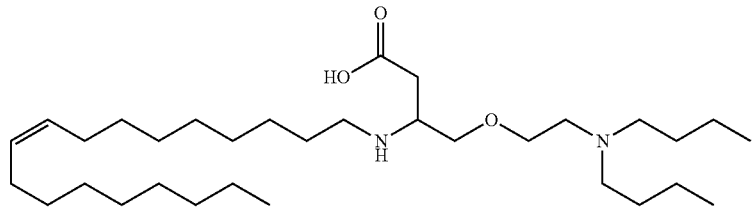

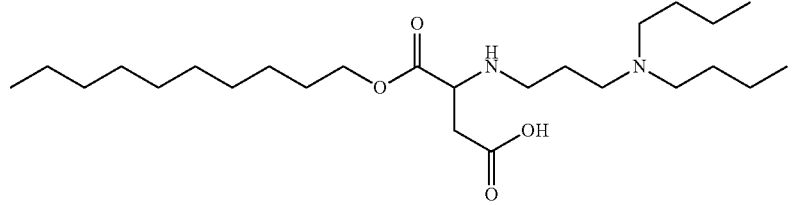

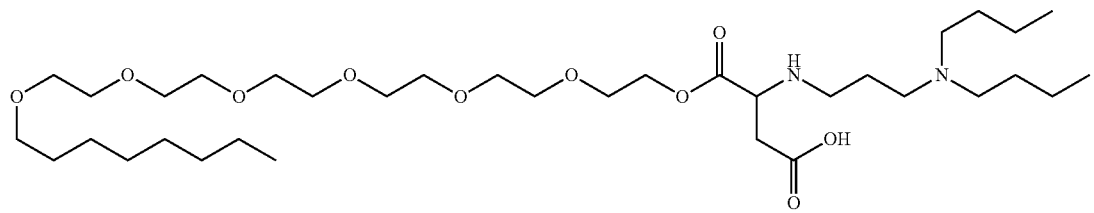

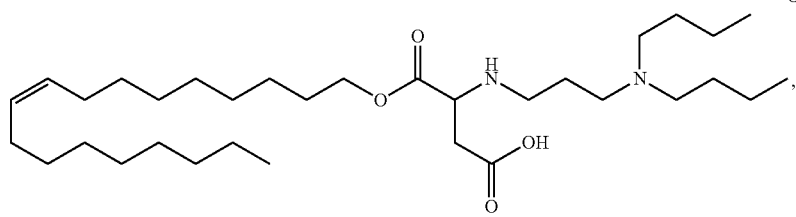

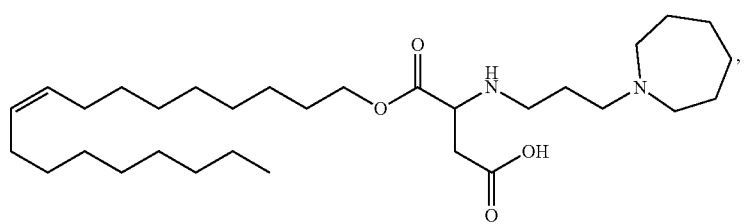

-continued

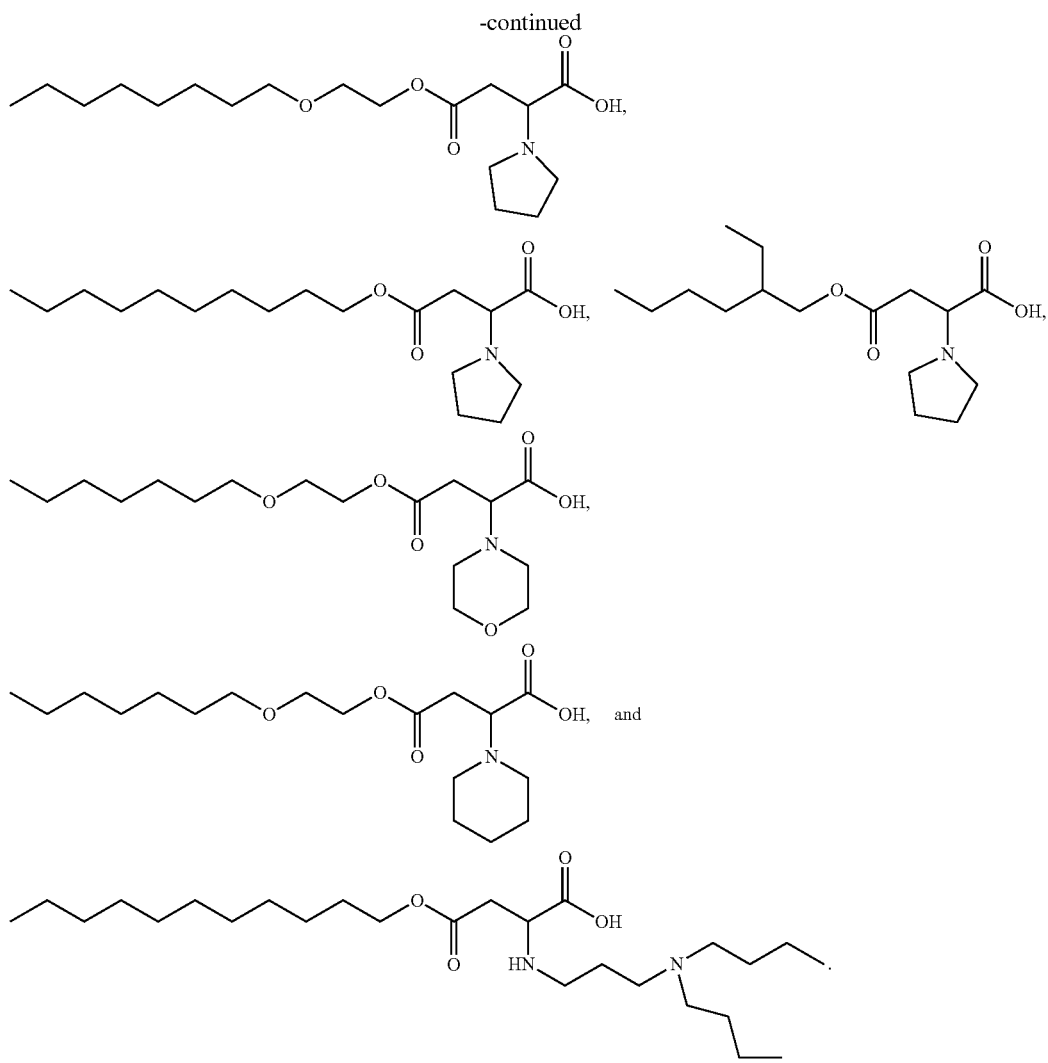

The compounds of formula (I) can be prepared by the following method of synthesis:

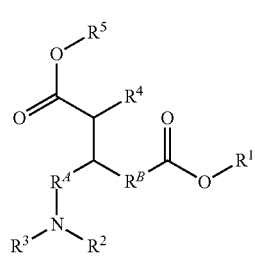

Formula (I)

the method comprising contacting an alcohol corresponding in structure to formula (II):

R$^1$—OH    Formula (II)

or

R$^5$—OH    Formula (II')

with an acid anhydride of formula (III) to produce an intermediate:

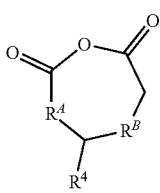

Formula (III)

and contacting the intermediate with an amine corresponding in structure to formula (IV):

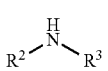

Formula (IV)

to produce a compound corresponding in structure to formula (I), wherein $R^A$ is a bond or a $C_1$-$C_4$ alkylene group; $R^B$ is a bond, a double bond, or a $C_1$-$C_4$ alkylene group; $R^1$ and $R^5$ are independently hydrogen, alkyl, alkenyl, alkynyl, cycloalkyl, aryl, or alkylaryl, wherein each group can optionally be substituted with an amine, a hydroxyl, or a carboxyl, and wherein each alkyl, alkenyl, alkynyl, cycloalkyl, or alkylaryl group can optionally have one or more —$CH_2$— groups replaced with an amine, a carbonyl, an ether, an amide, or an ester group; $R^2$ and $R^3$ are independently hydrogen, alkyl, alkenyl, or alkynyl, wherein each alkyl, alkenyl, or alkynyl group can optionally be substituted with an amine, a hydroxyl, or a carboxyl, and wherein each alkyl, alkenyl, or alkynyl group can optionally have one or more —$CH_2$— groups replaced with an amine, a carbonyl, an ether, an amide, or an ester group; or $R^2$ and $R^3$ together with the nitrogen they are attached to form a ring; and $R^4$ is hydrogen, alkyl, alkenyl, or alkynyl; provided that at least one of $R^1$ and $R^5$ is hydrogen when the other is other than hydrogen and when $R^2$ and $R^3$ together with the nitrogen they are attached to do not form a ring, at least one of $R^1$, $R^2$, $R^3$, and $R^5$ is a straight or branched alkyl or alkenyl group, wherein at least one of the —$CH_2$— groups is replaced by an amine or an ether group.

The method of synthesis described herein can have the acid anhydride of formula (III) comprise maleic anhydride, itaconic anhydride, citraconic anhydride, glutaconic anhydride, or a combination thereof.

The method of synthesis can further have the amine of formula (IV) comprise aminopropyl pyrrolidine, aminopropyl azepane, dibutylaminopropylamine (DBAPA), or a combination thereof.

The method of synthesis can also have the alcohol of formula (II) comprise 2-ethylhexanol, pentanol, hexanol, heptanol, octanol, decanol, dodecanol, isostearyl alcohol, 2-decyltetradecanol, 11-methyldodecanol, or a combination thereof.

The method of synthesis can have $R^1$ be straight or branched $C_6$-$C_{24}$ alkyl or $C_6$-$C_{24}$ alkenyl. Additionally, for the method of synthesis, $R^1$ can comprise 1 to 12 ethylene oxide units.

The method of synthesis described herein can have the compound of formula (I) be contacted with an organic acid to provide a salt of formula (I). Preferably, the organic acid comprises acetic acid, acrylic acid, or a combination thereof.

Preferably, the alcohols of formula (II) and (II') are the same.

The compounds can also have a structure corresponding to formula (V):

Formula (V)

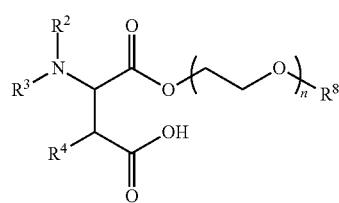

wherein $R^2$ and $R^3$ are independently alkyl, alkenyl, or alkynyl, wherein each alkyl, alkenyl, or alkynyl group can optionally be substituted with an amine, a hydroxyl, or a carboxyl, and wherein each alkyl, alkenyl, or alkynyl group can optionally have one or more —$CH_2$— groups replaced with an amine, a carbonyl, or an ether group; $R^4$ is hydrogen or alkyl; and $R^8$ is alkyl or alkenyl, wherein each group can optionally be substituted with an amine, a hydroxyl, or a carboxyl, and wherein each alkyl or alkenyl group can optionally have one or more —$CH_2$— groups replaced with an amine, a carbonyl, an ether, an amide, or an ester group; and n is an integer from 0 to 10.

The compounds of formula (V) can have $R^2$ and $R^3$ be alkyl; preferably, $R^2$ and $R^3$ are independently $C_1$-$C_{10}$ alkyl; more preferably, $R^2$ and $R^3$ are independently methyl, ethyl, propyl, butyl, pentyl, or hexyl.

The compounds of formula (V) can have $R^4$ be hydrogen or $C_1$-$C_6$ alkyl. Preferably, the compounds of formula (V) can have $R^4$ be hydrogen or methyl and more preferably, $R^4$ can be hydrogen.

The compounds of formula (V) can have $R^8$ be alkyl; preferably, $R^8$ can be $C_1$-$C_{20}$ alkyl; more preferably, $R^8$ can be $C_6$-$C_{20}$ alkyl.

The compounds of formula (V) can be:

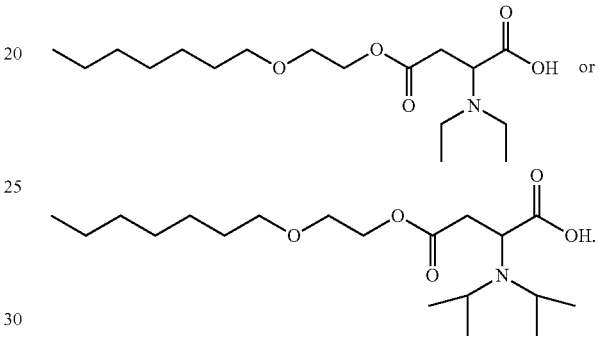

Also provided herein is a hydrate inhibitor composition comprising a hydrate-inhibiting effective amount of a compound of formula (I) or (V), or an acid, a free base, a zwitterion, or a salt thereof, as described in detail above.

The compounds of formula (I) can also be present in a hydrate inhibitor composition comprising a hydrate-inhibiting effective amount of a compound of formula (I), as described above, and methods of inhibiting formation of hydrate agglomerants in a fluid comprising water, a gas, and optionally a liquid hydrocarbon, the method comprising contacting the fluid with an effective amount of a hydrate inhibitor composition.

The hydrate inhibitor composition described herein can further comprise a thermodynamic hydrate inhibitor, a kinetic hydrate inhibitor, an anti-agglomerant, or a combination thereof.

The hydrate inhibitor composition described herein can further comprise a polar solvent, a non-polar solvent, or a combination thereof.

Representative polar solvents suitable for formulation with the hydrate inhibitor composition include water, brine, seawater, alcohols (including straight chain or branched aliphatic such as methanol, ethanol, propanol, isopropanol, butanol, 2-ethylhexanol, hexanol, octanol, decanol, 2-butoxyethanol, etc.), glycols and derivatives (ethylene glycol, 1,2-propylene glycol, 1,3-propylene glycol, ethylene glycol monobutyl ether, etc.), ketones (cyclohexanone, diisobutylketone), N-methylpyrrolidinone (NMP), N,N-dimethylformamide, and the like.

Representative non-polar solvents suitable for formulation with the hydrate inhibitor composition include aliphatics, such as pentane, hexane, cyclohexane, methylcyclohexane, heptane, decane, dodecane, diesel, and the like, and aromatics such as toluene, xylene, heavy aromatic naphtha, fatty acid derivatives (acids, esters, amides), and the like.

Preferred compounds of formula (I) can be prepared as detailed in the following reaction scheme.

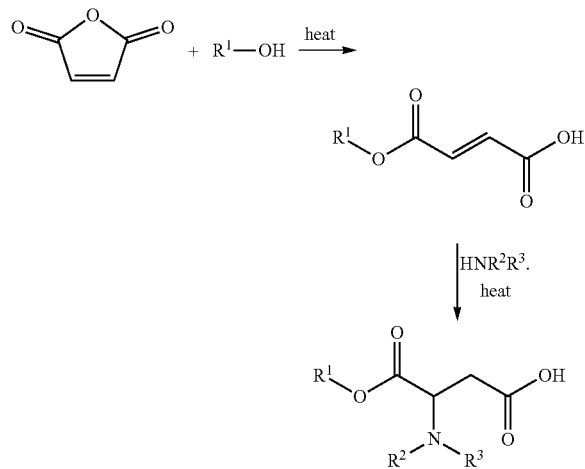

The composition comprising the hydrate inhibitor can be used in a method of inhibiting the formation of hydrate agglomerants in a fluid. Thus, also provided herein is a method of inhibiting the formation of hydrate agglomerants in a fluid (i.e., an aqueous medium), the method comprising water, gas, and optionally liquid hydrocarbon. The method comprises adding to the fluid an effective amount of a composition comprising one or more hydrate inhibitors (e.g., a hydrate inhibitor composition as described in detail above).

The hydrate inhibitor compositions and compounds of formula (I) can also be used in a method of inhibiting formation of hydrate agglomerants in a fluid comprising water, a gas, and optionally a liquid hydrocarbon, the method comprising contacting the fluid with an effective amount of a hydrate inhibitor composition or compound of formula (I) described herein.

The method of inhibiting formation of hydrate agglomerants can use an effective amount of the hydrate inhibitor composition of from about 0.1 to about 10 vol % based on the amount of water.

Various dosage amounts of the composition can be applied to the fluid to inhibit the formation of hydrate agglomerants. One of ordinary skill in the art would be able to calculate the amount of hydrate inhibitor or composition comprising a hydrate inhibitor for a given situation without undue experimentation. Factors that would be considered of importance in such calculations include, for example, the content of the fluid, percentage water cut, API gravity of the hydrocarbon, and test gas compositions. In this method, the effective amount can be, for example, from about 0.1 to about 25 vol %, from about 0.1 to about 23 vol %, from about 0.1 to about 20 vol %, from about 0.1 to about 18 vol %, from about 0.1 from about 15 vol %, from about 0.1 to about 13 vol %, from about 0.1 to about 10 vol %, from about 0.1 to about 8 vol %, from about 0.1 to about 5 vol %, from about 0.1 to about 4 vol %, from about 0.1 to about 3 vol %, from about 0.1 to about 2 vol %, or from about 0.1 to about 1 vol % based on the amount of water. Preferably, the effective amount is from about 0.1 to about 10 vol % based on the amount of water.

The method of inhibiting formation of hydrate agglomerants can be used for fluids contained in an oil or gas pipeline or oil or gas refinery. The fluid can be contained in an oil and gas pipeline. The fluid can also be contained in refineries, such as separation vessels, dehydration units, gas lines, and pipelines. For example, the fluid can be contained in an oil or gas pipeline refinery.

The method of inhibiting formation of hydrate agglomerants can have the water comprise a salinity of about 0% to about 25% weight/weight total dissolved solids (TDS).

Further, the composition comprising the hydrate inhibitor may be applied to a fluid that contains various levels of salinity. For example, the fluid can have a salinity of about 0% to about 50%, from about 0% to about 45%, from about 0% to about 40%, from about 0% to about 35%, from about 0% to about 30%, from about 0% to about 25%, from about 0% to about 20%, from about 0% to about 15%, from about 0% to about 10%, from about 0% to about 5%, from about 5% to about 50%, from about 10% to about 50%, from about 15% to about 50%, from about 15% to about 45%, from about 15% to about 40%, from about 15% to about 35%, from about 15% to about 30%, from about 15% to about 25%, or from about 15% to about 20% weight/weight total dissolved solids (TDS). Preferably, the fluid has a salinity of about 0% to about 25% weight/weight total dissolved solids (TDS). The fluid in which the disclosed compositions are applied can be contained in various types of apparatuses, especially those that transport a fluid from one location to another.

The composition comprising the hydrate inhibitor can be applied to a fluid that contains various levels of water cut. One of ordinary skill in the art understands that "water cut" refers to the percentage of water in a composition containing an oil and water mixture. As an example, the water cut can be from about 1% to about 80% weight/weight with respect to the hydrocarbon phase.

For some of the method of inhibiting formation of hydrate agglomerants, the composition is added downhole near a surface controlled sub-sea safety valve.

The compositions described herein can be applied to a fluid using various well-known methods at they may be applied at numerous different locations throughout a given system. For example, the composition comprising the hydrate inhibitor can be pumped into an oil/gas pipeline using an umbilical line. As an example, capillary string injection systems can be utilized to the deliver the compositions. U.S. Pat. No. 7,311,144 provides a description of an apparatus and methods relating to capillary injection, the disclosure of which is incorporated into the present application in its entirety.

The compositions and methods provided herein are effective to control gas hydrate formation and plugging during hydrocarbon production and transportation. The hydrate inhibitor may be injected prior to substantial formation of hydrates. An exemplary injection point for petroleum production operations is downhole near the surface controlled sub-sea safety valve. This ensures that during a shut-in, the product is able to disperse throughout the area where hydrates will occur. Treatment can also occur at other areas in the flowline, taking into account the density of the injected fluid. If the injection point is well above the hydrate formation depth, then the hydrate inhibitor may be formulated with a solvent having a density high enough that the inhibitor will sink in the flowline to collect at the water/oil interface. Moreover, the treatment can also be used in pipelines or anywhere in the system where the potential for hydrate formation exists.

The compounds disclosed herein have been shown to have acceptable toxicity results in that a concentration of greater than 10 ppm is tolerated by tested marine species.

Further, the compounds disclosed herein can also have corrosion inhibition properties.

The composition comprising the hydrate inhibitor can be introduced into the fluid by any means suitable for ensuring dispersal of the hydrate inhibitor through the fluid being treated. Typically, the composition comprising the hydrate inhibitor is injected using mechanical equipment such as chemical injection pumps, piping tees, injection fittings, and the like. The composition comprising the hydrate inhibitor can be injected as prepared or formulated in one or more additional polar or non-polar solvents, depending upon the application and requirements.

The composition can further comprise a thermodynamic hydrate inhibitor, a kinetic hydrate inhibitor, an anti-agglomerant, or a combination thereof.

The composition can still further comprise a component selected from the group consisting of an organic solvent, a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, and a combination thereof.

The hydrate inhibitor composition described herein can also further comprise an organic solvent, a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof.

The component of the composition can comprise an organic solvent. The composition can comprise from about 1 to 80 wt. %, from about 5 to 50 wt. %, or from about 10 to 35 wt. % of the one or more organic solvents, based on total weight of the composition. The organic solvent can comprise an alcohol, a hydrocarbon, a ketone, an ether, an alkylene glycol, a glycol ether, an amide, a nitrile, a sulfoxide, an ester, or a combination thereof. Examples of suitable organic solvents include, but are not limited to, methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

The component of the composition can comprise a corrosion inhibitor. The composition can comprise from about 0.1 to 20 wt. %, 0.1 to 10 wt. %, or 0.1 to 5 wt. % of the corrosion inhibitors, based on total weight of the composition. A composition described herein can comprise from 0.1 to 10 percent by weight of the corrosion inhibitors, based on total weight of the composition. The composition can comprise 1.0 wt %, 1.5 wt %, 2.0 wt %, 2.5 wt %, 3.0 wt %, 3.5 wt %, 4.0 wt %, 4.5 wt %, 5.0 wt %, 5.5 wt %, 6.0 wt %, 6.5 wt %, 7.0 wt %, 7.5 wt %, 8.0 wt %, 8.5 wt %, 9.0 wt %, 9.5 wt %, 10.0 wt %, 10.5 wt %, 11.0 wt %, 11.5 wt %, 12.0 wt %, 12.5 wt %, 13.0 wt %, 13.5 wt %, 14.0 wt %, 14.5 wt %, or 15.0 wt % by weight of the corrosion inhibitors, based on total weight of the composition. Each system can have its own requirements, and the weight percent of one or more additional corrosion inhibitors in the composition can vary with the system in which it is used.

The corrosion inhibitor can comprise an imidazoline compound, a quaternary ammonium compound, a pyridinium compound, or a combination thereof.

The corrosion inhibitor component can comprise an imidazoline. The imidazoline can be, for example, imidazoline derived from a diamine, such as ethylene diamine (EDA), diethylene triamine (DETA), triethylene tetraamine (TETA) etc. and a long chain fatty acid such as tall oil fatty acid (TOFA). The imidazoline can be an imidazoline of Formula (I) or an imidazoline derivative. Representative imidazoline derivatives include an imidazolinium compound of Formula (II) or a bis-quaternized compound of Formula (III).

The corrosion inhibitor component can include an imidazoline of Formula (I):

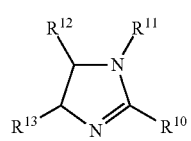

(I)

wherein $R^{10}$ is a $C_1$-$C_{20}$ alkyl or a $C_1$-$C_{20}$ alkoxyalkyl group; $R^{11}$ is hydrogen, $C_1$-$C_6$ alkyl, $C_1$-$C_6$ hydroxyalkyl, or $C_1$-$C_6$ arylalkyl; and $R^{12}$ and $R^{13}$ are independently hydrogen or a $C_1$-$C_6$ alkyl group. Preferably, the imidazoline includes an $R^{10}$ which is the alkyl mixture typical in tall oil fatty acid (TOFA), and $R^{11}$, $R^{12}$ and $R^{13}$ are each hydrogen.

The corrosion inhibitor component can include an imidazolinium compound of Formula (II):

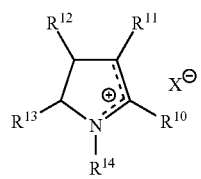

(II)

wherein $R^{10}$ is a $C_1$-$C_{20}$ alkyl or a $C_1$-$C_{20}$ alkoxyalkyl group; $R^{11}$ and $R^{14}$ are independently hydrogen, $C_1$-$C_6$ alkyl, $C_1$-$C_6$ hydroxyalkyl, or $C_1$-$C_6$ arylalkyl; $R^{12}$ and $R^{13}$ are independently hydrogen or a $C_1$-$C_6$ alkyl group; and $X^-$ is a halide (such as chloride, bromide, or iodide), carbonate, sulfonate, phosphate, or the anion of an organic carboxylic acid (such as acetate). Preferably, the imidazolinium compound includes 1-benzyl-1-(2-hydroxyethyl)-2-tall-oil-2-imidazolinium chloride.

The corrosion inhibitor can comprise a bis-quaternized compound having the formula (III):

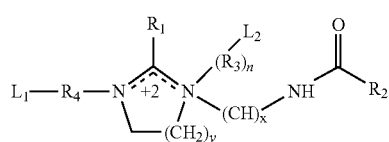

(III)

wherein $R_1$ and $R_2$ are each independently unsubstituted branched, chain or ring alkyl or alkenyl having from 1 to about 29 carbon atoms; partially or fully oxygenized, sulfurized, and/or phosphorylized branched, chain, or ring alkyl or alkenyl having from 1 to about 29 carbon atoms; or a combination thereof; $R_3$ and $R_4$ are each independently unsubstituted branched, chain or ring alkylene or alkenylene having from 1 to about 29 carbon atoms; partially or fully oxygenized, sulfurized, and/or phosphorylized branched, chain, or ring alkylene or alkenylene having from 1 to about 29 carbon atoms; or a combination thereof; $L_1$ and $L_2$ are each independently absent, H, —COOH, —SO$_3$H, —PO$_3$H$_2$, —COOR$_5$, —CONH$_2$, —CONHR$_5$, or —CON(R$_5$)$_2$; $R_5$ is each independently a branched or unbranched alkyl, aryl, alkylaryl, alkylheteroaryl, cycloalkyl, or heteroaryl group having from 1 to about 10 carbon atoms; n is 0 or 1, and when n is 0, $L_2$ is absent or H; x is from 1 to about 10; and y is from 1 to about 5. Preferably, $R_1$ and $R_2$ are each independently $C_6$-$C_{22}$ alkyl, $C_6$-$C_{20}$ alkyl, $C_{12}$-$C_{18}$ alkyl, $C_{16}$-$C_{18}$ alkyl, or a combination thereof; $R_3$ and $R_4$ are $C_1$-$C_{10}$ alkylene, $C_2$-$C_8$ alkylene, $C_2$-$C_6$ alkylene, or $C_2$-$C_3$ alkylene; n is 0 or 1; x is 2; y is 1; $R_3$ and $R_4$ are —C$_2$H$_2$—; $L_1$ is —COOH, —SO$_3$H, or —PO$_3$H$_2$; and $L_2$ is absent, H, —COOH, —SO$_3$H, or —PO$_3$H$_2$. For example, $R_1$ and $R_2$ can be derived from a mixture of tall oil fatty acids and are predominantly a mixture of $C_{17}H_{33}$ and $C_{17}H_{31}$ or can be $C_{16}$-$C_{18}$ alkyl; $R^3$ and $R^4$ can be $C_2$-$C_3$ alkylene such as —C$_2$H$_2$—; n is 1 and $L_2$ is —COOH or n is 0 and $L_2$ is absent or H; x is 2; y is 1; $R_3$ and $R_4$ are —C$_2$H$_2$—; and $L_1$ is —COOH.

It should be appreciated that the number of carbon atoms specified for each group of formula (III) refers to the main chain of carbon atoms and does not include carbon atoms that may be contributed by substituents.

The corrosion inhibitor can comprise a bis-quaternized imidazoline compound having the formula (III) wherein $R_1$ and $R_2$ are each independently $C_6$-$C_{22}$ alkyl, $C_6$-$C_{20}$ alkyl, $C_{12}$-$C_{18}$ alkyl, or $C_{16}$-$C_{18}$ alkyl or a combination thereof; $R_4$ is $C_1$-$C_{10}$ alkylene, $C_2$-$C_8$ alkylene, $C_2$-$C_6$ alkylene, or $C_2$-$C_3$ alkylene; x is 2; y is 1; n is 0; $L_1$ is —COOH, —SO$_3$H, or —PO$_3$H$_2$; and $L_2$ is absent or H. Preferably, a bis-quaternized compound has the formula (III) wherein $R_1$ and $R_2$ are each independently $C_{16}$-$C_{18}$ alkyl; $R^4$ is —C$_2$H$_2$—; x is 2; y is 1; n is 0; $L_1$ is —COOH, —SO$_3$H, or —PO$_3$H$_2$ and $L_2$ is absent or H.

The corrosion inhibitor can be a quaternary ammonium compound of Formula (IV):

(IV)

wherein $R_1$, $R_2$, and $R_3$ are independently $C_1$ to $C_{20}$ alkyl, $R_4$ is methyl or benzyl, and X$^-$ is a halide or methosulfate.

Suitable alkyl, hydroxyalkyl, alkylaryl, arylalkyl or aryl amine quaternary salts include those alkylaryl, arylalkyl and aryl amine quaternary salts of the formula [N$^+$R$^{5a}$R$^{6a}$R$^{7a}$R$^{8a}$][X$^-$] wherein R$^{5a}$, R$^{6a}$, R$^{7a}$, and R$^{8a}$ contain one to 18 carbon atoms, and X is Cl, Br or I. For the quaternary salts, R$^{5a}$, R$^{6a}$, R$^{7a}$, and R$^{8a}$ can each be independently selected from the group consisting of alkyl (e.g., $C_1$-$C_{18}$ alkyl), hydroxyalkyl (e.g., $C_1$-$C_{18}$ hydroxyalkyl), and arylalkyl (e.g., benzyl). The mono or polycyclic aromatic amine salt with an alkyl or alkylaryl halide include salts of the formula [N$^+$R$^{5a}$R$^{6a}$R$^{7a}$R$^{8a}$][X$^-$] wherein R$^{5a}$, R$^{6a}$, R$^{7a}$, and R$^{8a}$ contain one to 18 carbon atoms and at least one aryl group, and X is Cl, Br or I.

Suitable quaternary ammonium salts include, but are not limited to, a tetramethyl ammonium salt, a tetraethyl ammonium salt, a tetrapropyl ammonium salt, a tetrabutyl ammonium salt, a tetrahexyl ammonium salt, a tetraoctyl ammonium salt, a benzyltrimethyl ammonium salt, a benzyltriethyl ammonium salt, a phenyltrimethyl ammonium salt, a phenyltriethyl ammonium salt, a cetyl benzyldimethyl ammonium salt, a hexadecyl trimethyl ammonium salt, a dimethyl alkyl benzyl quaternary ammonium salt, a monomethyl dialkyl benzyl quaternary ammonium salt, or a trialkyl benzyl quaternary ammonium salt, wherein the alkyl group has about 6 to about 24 carbon atoms, about 10 and about 18 carbon atoms, or about 12 to about 16 carbon atoms. The quaternary ammonium salt can be a benzyl trialkyl quaternary ammonium salt, a benzyl triethanolamine quaternary ammonium salt, or a benzyl dimethylaminoethanolamine quaternary ammonium salt.

The corrosion inhibitor component can comprise a pyridinium salt such as those represented by Formula (V):

(V)

wherein $R^9$ is an alkyl group, an aryl group, or an arylalkyl group, wherein said alkyl groups have from 1 to about 18 carbon atoms and X$^-$ is a halide such as chloride, bromide, or iodide. Among these compounds are alkyl pyridinium salts and alkyl pyridinium benzyl quats. Exemplary compounds include methyl pyridinium chloride, ethyl pyridinium chloride, propyl pyridinium chloride, butyl pyridinium chloride, octyl pyridinium chloride, decyl pyridinium chloride, lauryl pyridinium chloride, cetyl pyridinium chloride, benzyl pyridinium chloride and an alkyl benzyl pyridinium chloride, preferably wherein the alkyl is a $C_1$-$C_6$ hydrocarbyl group. Preferably, the pyridinium compound includes benzyl pyridinium chloride.

The corrosion inhibitor components can include additional corrosion inhibitors such as phosphate esters, monomeric or oligomeric fatty acids, or alkoxylated amines.

The corrosion inhibitor component can comprise a phosphate ester.

Suitable mono-, di- and tri-alkyl as well as alkylaryl phosphate esters and phosphate esters of mono, di, and triethanolamine typically contain between from 1 to about 18 carbon atoms. Preferred mono-, di- and trialkyl phosphate esters, alkylaryl or arylalkyl phosphate esters are those prepared by reacting a $C_3$-$C_{18}$ aliphatic alcohol with phosphorous pentoxide. The phosphate intermediate interchanges its ester groups with triethylphosphate producing a more broad distribution of alkyl phosphate esters.

Alternatively, the phosphate ester can be made by admixing with an alkyl diester, a mixture of low molecular weight alkyl alcohols or diols. The low molecular weight alkyl alcohols or diols preferably include $C_6$ to $C_{10}$ alcohols or diols. Further, phosphate esters of polyols and their salts containing one or more 2-hydroxyethyl groups, and hydroxylamine phosphate esters obtained by reacting polyphosphoric acid or phosphorus pentoxide with hydroxylamines such as diethanolamine or triethanolamine are preferred.

The corrosion inhibitor component can include a monomeric or oligomeric fatty acid. Preferred monomeric or oligomeric fatty acids are $C_{14}$-$C_{22}$ saturated and unsaturated fatty acids as well as dimer, trimer and oligomer products obtained by polymerizing one or more of such fatty acids.

The corrosion inhibitor component can comprise an alkoxylated amine. The alkoxylated amine can be an ethoxylated alkyl amine. The alkoxylated amine can be ethoxylated tallow amine.

The component of the composition can comprise an organic sulfur compound, such as a mercaptoalkyl alcohol, mercaptoacetic acid, thioglycolic acid, 3,3'-dithiodipropionic acid, sodium thiosulfate, thiourea, L-cysteine, tert-butyl mercaptan, sodium thiosulfate, ammonium thiosulfate, sodium thiocyanate, ammonium thiocyanate, sodium metabisulfite, or a combination thereof. Preferably, the mercaptoalkyl alcohol comprises 2-mercaptoethanol. The organic sulfur compound can constitute 0.5 to 15 wt. % of the composition, based on total weight of the composition, preferably about 1 to about 10 wt. % and more preferably about 1 to about 5 wt. %. The organic sulfur compound can constitute 1, 2, 3, 4, 5, 6, 7, 8, 9, 10, 11, 12, 13, 14 or 15 wt. % of the composition.

The composition can be substantially free of or free of any organic sulfur compound other than the compound of formula (1). A composition is substantially free of any organic sulfur compound if it contains an amount of organic sulfur compound below the amount that will produce hydrogen sulfide gas upon storage at a temperature of 25° C. and ambient pressure.

The component of the composition can further include a demulsifier. Preferably, the demulsifier comprises an oxyalkylate polymer, such as a polyalkylene glycol. The demulsifier can constitute from about 0.1 to 10 wt. %, from about 0.5 to 5 wt. %, or from about 0.5 to 4 wt. % of the composition, based on total weight of the composition. The demulsifier can constitute 0.5, 1, 1.5, 2, 2.5, 3, 3.5, 4, 4.5 or 5 wt. % of the composition.

The component of the composition can include an asphaltene inhibitor. The composition can comprise from about 0.1 to 10 wt. %, from about 0.1 to 5 wt. %, or from about 0.5 to 4 wt. % of an asphaltene inhibitor, based on total weight of the composition. Suitable asphaltene inhibitors include, but are not limited to, aliphatic sulfonic acids; alkyl aryl sulfonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

The component of the composition can include a paraffin inhibitor. The composition can comprise from about 0.1 to 10 wt. %, from about 0.1 to 5 wt. %, or from about 0.5 to 4 wt. % of a paraffin inhibitor, based on total weight of the composition. Suitable paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable paraffin dispersants include, but are not limited to, dodecyl benzene sulfonate, oxyalkylated alkylphenols, and oxyalkylated alkylphenolic resins.

The component of the composition can include a scale inhibitor. The composition can comprise from about 0.1 to 20 wt. %, from about 0.5 to 10 wt. %, or from about 1 to 10 wt. % of a scale inhibitor, based on total weight of the composition. Suitable scale inhibitors include, but are not limited to, phosphates, phosphate esters, phosphoric acids, phosphonates, phosphonic acids, polyacrylamides, salts of acrylamidomethyl propane sulfonate/acrylic acid copolymer (AMPS/AA), phosphinated maleic copolymer (PHOS/MA), and salts of a polymaleic acid/acrylic acid/acrylamidomethyl propane sulfonate terpolymer (PMA/AA/AMPS).

The component of the composition can include an emulsifier. The composition can comprise from about 0.1 to 10 wt. %, from about 0.5 to 5 wt. %, or from about 0.5 to 4 wt. % of an emulsifier, based on total weight of the composition. Suitable emulsifiers include, but are not limited to, salts of carboxylic acids, products of acylation reactions between carboxylic acids or carboxylic anhydrides and amines, and alkyl, acyl and amide derivatives of saccharides (alkyl-saccharide emulsifiers).

The component of the composition can include a water clarifier. The composition can comprise from about 0.1 to 10 wt. %, from about 0.5 to 5 wt. %, or from about 0.5 to 4 wt. % of a water clarifier, based on total weight of the composition. Suitable water clarifiers include, but are not limited to, inorganic metal salts such as alum, aluminum chloride, and aluminum chlorohydrate, or organic polymers such as acrylic acid based polymers, acrylamide based polymers, polymerized amines, alkanolamines, thiocarbamates, and cationic polymers such as diallyldimethylammonium chloride (DADMAC).

The component of the composition can include a dispersant. The composition can comprise from about 0.1 to 10 wt. %, from about 0.5 to 5 wt. %, or from about 0.5 to 4 wt. % of a dispersant, based on total weight of the composition. Suitable dispersants include, but are not limited to, aliphatic phosphonic acids with 2-50 carbons, such as hydroxyethyl diphosphonic acid, and aminoalkyl phosphonic acids, e.g. polyaminomethylene phosphonates with 2-10 N atoms e.g. each bearing at least one methylene phosphonic acid group; examples of the latter are ethylenediamine tetra(methylene phosphonate), diethylenetriamine penta(methylene phosphonate), and the triamine- and tetramine-polymethylene phosphonates with 2-4 methylene groups between each N atom, at least 2 of the numbers of methylene groups in each phosphonate being different. Other suitable dispersion agents include lignin, or derivatives of lignin such as lignosulfonate and naphthalene sulfonic acid and derivatives.

The component of the composition can include an emulsion breaker. The composition can comprise from about 0.1 to 10 wt. %, from about 0.5 to 5 wt. %, or from about 0.5 to 4 wt. % of an emulsion breaker, based on total weight of the composition. Suitable emulsion breakers include, but are not limited to, dodecylbenzylsulfonic acid (DDBSA), the sodium salt of xylenesulfonic acid (NAXSA), epoxylated and propoxylated compounds, anionic, cationic and non-ionic surfactants, and resins, such as phenolic and epoxide resins.

The component of the composition can include a hydrogen sulfide scavenger. The composition can comprise from about 1 to 50 wt. %, from about 1 to 40 wt. %, or from about 1 to 30 wt. % of a hydrogen sulfide scavenger, based on total weight of the composition. Suitable additional hydrogen sulfide scavengers include, but are not limited to, oxidants (e.g., inorganic peroxides such as sodium peroxide or chlorine dioxide); aldehydes (e.g., of 1-10 carbons such as formaldehyde, glyoxal, glutaraldehyde, acrolein, or methacrolein; triazines (e.g., monoethanolamine triazine, monomethylamine triazine, and triazines from multiple amines or mixtures thereof); condensation products of secondary or tertiary amines and aldehydes, and condensation products of alkyl alcohols and aldehydes.

The component of the composition can include a gas hydrate inhibitor. The composition can comprise from about 0.1 to 25 wt. %, from about 0.1 to 20 wt. %, or from about 0.3 to 20 wt. % of a gas hydrate inhibitor, based on total weight of the composition. Suitable gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, sodium chloride, potassium chloride, calcium chloride, magnesium chloride, sodium bromide, formate brines (e.g. potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate).

The component of the composition can include a kinetic hydrate inhibitor. The composition can comprise from about 5 to 30 wt. %, from about 5 to 25 wt. %, or from about 10 to 25 wt. % of a kinetic hydrate inhibitor, based on total weight of the composition. Suitable kinetic hydrate inhibitors and anti-agglomerates include, but are not limited to, polymers and copolymers, polysaccharides (such as hydroxyethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), surfactants (such as fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines), hydrocarbon based dispersants (such as lignosulfonates, iminodisuccinates, polyaspartates), amino acids, and proteins.

The component of the composition can include a biocide. The composition can comprise from about 0.1 to 10 wt. %, from about 0.5 to 5 wt. %, or from about 0.5 to 4 wt. % of a biocide, based on total weight of the composition. Suitable biocides include, but are not limited to, oxidizing and non-oxidizing biocides. Suitable non-oxidizing biocides include, for example, aldehydes (e.g., formaldehyde, glutaraldehyde, and acrolein), amine-type compounds (e.g., quaternary amine compounds and cocodiamine), halogenated compounds (e.g., 2-bromo-2-nitropropane-3-diol (Bronopol) and 2-2-dibromo-3-nitrilopropionamide (DBNPA)), sulfur compounds (e.g., isothiazolone, carbamates, and metronidazole), and quaternary phosphonium salts (e.g., tetrakis(hydroxymethyl)-phosphonium sulfate (THPS)). Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, and peroxides.

The component of the composition can include a pH modifier. The composition can comprise from about 0.1 to 20 wt. %, from about 0.5 to 10 wt. %, or from about 0.5 to 5 wt. % of a pH modifier, based on total weight of the composition. Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include sodium hydroxide, potassium hydroxide, calcium hydroxide, calcium oxide, sodium carbonate, potassium carbonate, sodium bicarbonate, potassium bicarbonate, magnesium oxide, and magnesium hydroxide.

The component of the composition can include a surfactant. The composition can comprise from about 0.1 to 10 wt. %, from about 0.5 to 5 wt. %, or from about 0.5 to 4 wt. % of a surfactant, based on total weight of the composition. Suitable surfactants include, but are not limited to, anionic surfactants and nonionic surfactants. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Nonionic surfactants include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopropionates and amphodipropionates, and alkylim inodipropionate.

Hydrate inhibitor compositions made as described herein can further include additional functional agents or additives that provide a beneficial property. For example, additional agents or additives can be sequestrants, solubilizers, lubricants, buffers, cleaning agents, rinse aids, preservatives, binders, thickeners or other viscosity modifiers, processing aids, carriers, water-conditioning agents, foam inhibitors or foam generators, threshold agents or systems, aesthetic enhancing agents (i.e., dyes, odorants, perfumes), or other additives suitable for formulation with a corrosion inhibitor composition, and mixtures thereof. Additional agents or additives will vary according to the particular corrosion inhibitor composition being manufactured and its intend use as one skilled in the art will appreciate.

Alternatively, the compositions can not contain any of the additional agents or additives.

Additionally, the compounds of formula (I) or hydrate inhibitor compositions described herein can be formulated into a treatment fluid comprising the following components. These formulations include the ranges of the components listed and can optionally include additional agents.

| Component | 1 | 2 | 3 | 4 | 5 | 6 | 7 | 8 | 9 | 10 | 11 | 12 |
|---|---|---|---|---|---|---|---|---|---|---|---|---|
| Compound of formula (I) | 30-90 | 30-90 | 30-90 | 30-90 | 30-90 | 30-90 | 65-85 | 65-85 | 65-85 | 65-85 | 65-85 | 30-90 |
| Organic solvent | 10-35 | | | | | | 10-35 | | | | | 10-35 |
| Corrosion inhibitor | 0.1-20 | 0.1-20 | | | | | 0.1-20 | 0.1-20 | | | | 0.1-20 |
| Asphaltene inhibitor | 0.1-5 | 0.1-5 | 0.1-5 | 0.1-5 | | | 0.1-5 | 0.1-5 | 0.1-5 | | | 0.1-5 |
| Paraffin inhibitor | | | | | | | | | | | | |
| Scale inhibitor | 1-10 | 1-10 | 1-10 | 1-10 | 1-10 | | 1-10 | 1-10 | 1-10 | 1-10 | | 1-10 |
| Emulsifier | | | | | | | | | | | | |
| Water clarifier | | | | | | | | | | | | |
| Dispersant | | | | | | | | | | | | |
| Emulsion breaker | | | | | | | | | | | | |
| Additional gas hydrate inhibitor | | | | | | | | | | | | 0.1-25 |
| Biocide | 0.5-5 | 0.5-5 | 0.5-5 | 0.5-5 | 0.5-5 | 0.5-5 | 0.5-5 | 0.5-5 | 0.5-5 | 0.5-5 | 0.5-5 | |
| pH modifier | | | | | | | | | | | | |
| Surfactant | | | | | | | | | | | | |

| Component | 13 | 14 | 15 | 16 | 17 | 18 | 19 | 20 | 21 | 22 | 23 | 24 |
|---|---|---|---|---|---|---|---|---|---|---|---|---|
| Compound of formula (I) | 30-90 | 30-90 | 30-90 | 30-90 | 30-90 | 30-90 | 65-85 | 65-85 | 65-85 | 65-85 | 65-85 | 65-85 |
| Organic solvent | | | | | | | | | | | | |
| Corrosion inhibitor | 0.1-20 | 0.1-20 | 0.1-20 | 0.1-20 | 0.1-20 | 0.1-20 | 0.1-20 | 0.1-20 | 0.1-20 | 0.1-20 | 0.1-20 | 0.1-20 |
| Asphaltene inhibitor | 0.1-5 | | | | | | 0.1-5 | | | | | |
| Paraffin inhibitor | | | | | | | | | | | | |
| Scale inhibitor | 1-10 | 1-10 | | 1-10 | | | 1-10 | 1-10 | | | | 1-10 |
| Emulsifier | | | | | | | | | | | | |
| Water clarifier | | | | | | | | | | | | |
| Dispersant | | | | | | | | | | | | |
| Emulsion breaker | | | | | | | | | | | | |
| Additional gas hydrate inhibitor | 0.1-25 | 0.1-25 | 0.1-25 | | | | 0.1-25 | 0.1-25 | 0.1-25 | | 0.1-25 | |
| Biocide | | | | | 0.5-5 | 0.5-5 | 0.5-5 | 0.5-5 | 0.5-5 | 0.5-5 | 0.5-5 | |
| pH modifier | | | | | | | | | | | | |
| Surfactant | | | | | | | | | | | | |

Unless otherwise indicated, an alkyl group as described herein alone or as part of another group is an optionally substituted linear saturated monovalent hydrocarbon substituent containing from one to sixty carbon atoms and preferably one to thirty carbon atoms in the main chain or eight to thirty carbon atoms in the main chain, or an optionally substituted branched saturated monovalent hydrocarbon substituent containing three to sixty carbon atoms, and preferably eight to thirty carbon atoms in the main chain. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

The term alkoxy as used herein or alone or as part of another group is an —OR group, wherein the R group is a substituted or unsubstituted alkyl group as defined herein.

The terms "aryl" or "ar" as used herein alone or as part of another group (e.g., aralkyl) denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl. The term "aryl" also includes heteroaryl.

The term "substituted" as in "substituted aryl," "substituted alkyl," and the like, means that in the group in question (i.e., the alkyl, aryl or other group that follows the term), at least one hydrogen atom bound to a carbon atom is replaced with one or more substituent groups such as hydroxy (—OH), alkylthio, phosphino, amido (—CON($R_A$)($R_B$), wherein $R_A$ and $R_B$ are independently hydrogen, alkyl, or aryl), amino(—N($R_A$)($R_B$), wherein $R_A$ and $R_B$ are independently hydrogen, alkyl, or aryl), halo (fluoro, chloro, bromo, or iodo), silyl, nitro (—$NO_2$), an ether (—$OR_A$ wherein $R_A$ is alkyl or aryl), an ester (—OC(O)$R_A$ wherein $R_A$ is alkyl or aryl), keto (—C(O)R wherein $R_A$ is alkyl or aryl), heterocyclo, and the like. When the term "substituted" introduces a list of possible substituted groups, it is intended that the term apply to every member of that group. That is, the phrase "optionally substituted alkyl or aryl" is to be interpreted as "optionally substituted alkyl or optionally substituted aryl."

The term "heterocyclo," "heterocycle," or "heterocyclyl," as used herein, refers to a monocyclic, bicyclic, or tricyclic group containing 1 to 4 heteroatoms selected from N, O, $S(O)_n$, $P(O)_n$, $PR^z$, NH or $NR^z$, wherein $R^z$ is a suitable substituent. Heterocyclic groups optionally contain one or two double bonds. Heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Examples of monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4- oxazin-2-yl, and 1,2,5-oxathiazin-4-yl. Heterocyclic groups can be unsubstituted or substituted by one or more suitable substituents, preferably 1 to 3 suitable substituents, as defined above.

Having described the invention in detail, it will be apparent that modifications and variations are possible without departing from the scope of the invention defined in the appended claims.

EXAMPLES

The following non-limiting examples are provided to further illustrate the present invention.

Example 1: Reaction of Maleic Anhydride-Alcohol, 2-Ethyl Hexanol, and Pyrrolidine Maleic anhydride (5.00 g) and 2-ethyl hexanol (6.64 g) were added to a vial with a stir bar. At ambient temperature, the maleic anhydride in the solution of 2-ethyl hexanol was solid. The mixture was heated to 60° C. with stirring and left at 60° C. overnight. After stirring overnight at 60° C., the solution was free-flowing and homogenous with dispersed solid particles. Thin layer chromatography (TLC) showed that 2-ethyl hexanol was consumed in the reaction.

The vial was heated to 80° C. and the solid particulate dissolved. After stirring for approximately eight hours at 80° C., approximately 4.5 mL of pyrrolidine (4.26 g) was added. A sub-stoichiometric amount of pyrrolidine was added so that the reaction could be better monitored. The reaction was then cooled to ambient temperature and solidified. Generally, the reaction proceeded as depicted in Scheme 1.

Scheme 1.
Reaction of Maleic Anhydride, 2-Ethyl Hexanol, and Pyrrolidine

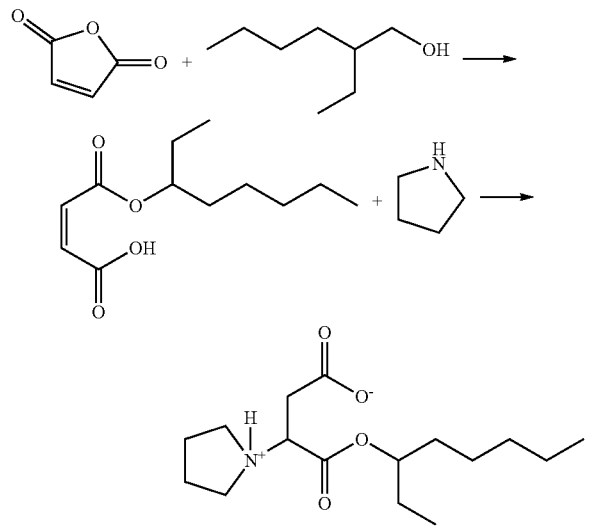

Two TLC plates were processed with separate solvents: a 5:1 mixture of heptane to ethyl acetate and an 8:2 mixture of acetone to water. The TLC plate was stained with ninhydrin to show amines and bromocresol green to see acids.

Pyrrolidine gave a blue color by TLC. The alcohol turned a blue color with bromocresol green. Ninhydrin gives excellent spots with amines, but is difficult to visualize with alcohol. The acetone/water solvent is good for visualizing the second reaction step. Thin layer chromatography (TLC) was utilized to identify extent of reaction. TLC was performed using a variety of different techniques, most notably 5:1 heptane: ethyl acetate or 8:2 acetone: water as the mobile phase, and utilizing bromocresol green or ninhydrin as a staining medium.

Example 2: Reaction of Maleic Anhydride and Various Alcohols and Amines

The reagents used in this Example and corresponding amounts of each are listed in Table 1.

TABLE 1

Reagents for Reaction of Maleic Anhydride with Various Alcohols and Amines

| Reaction | Amount Maleic Anhydride (g) | Alcohol | Amount Alcohol (mL) | Amine | Amount Amine (mL) |
|---|---|---|---|---|---|
| 1 | 0.88 | 1-hexanol | 1.12 | Pyrrolidine | 0.74 |
| 2 | 0.88 | 1-hexanol | 1.12 | Dibutylamine | 1.51 |
| 3 | 2.00 | ALFOL 810 | 3.56 | Pyrrolidine | 1.67 |
| 4 | 2.00 | ALFOL 810 | 3.56 | Dibutylamine | 3.44 |
| 5 | 2.00 | ALFOL 10 | 3.88 | Pyrrolidine | 1.67 |
| 6 | 2.00 | ALFOL 10 | 3.88 | Dibutylamine | 3.44 |
| 7 | 2.00 | ALFOL 1214 | 4.85 | Pyrrolidine | 1.67 |
| 8 | 2.00 | ALFOL 1214 | 4.85 | Dibutylamine | 3.44 |

Generally, the procedure for each reaction was as follows. The alcohol and maleic anhydride were added to a 20-mL vial with cross-shaped stir bar at ambient temperature. The mixture was stirred at 250 rpm and heated to 80° C. The maleic anhydride dissolved upon heating.

At reaction start time, a significant amount of maleic anhydride was present in the mixture, as determined by TLC. At one hour, some maleic anhydride was remaining, but there was a significant reduction in concentration. 1-hexanol proved difficult to visualize on the TLC plate. At two hours, it appeared as though all maleic anhydride was consumed, as determined by TLC. At 2.5 hours, the reactions were cooled to 25° C.

Reactions 7 and 8 became solid at temperatures of 45° C. and cooler, so the reaction temperature was increased to 60° C. At 60° C., reaction 1 became a solid gel after addition of the amine, so the reaction temperature was further increased to 80° C. Stir rate was decreased to 100 rpm due to increased sheer.

A 8:2 chloroform to methanol solvent was used for TLC development.

Example 3: Reaction of Maleic Anhydride, 2-Ethyl Hexanol, Isopropanol, and Pyrrolidine Maleic anhydride (3.28 g) and 2-ethyl hexanol (4.35 g) were added to a 40-mL vial with a cross-shaped stir bar. The mixture was stirred at 250 rpm and heated to 60° C. for three hours. The reaction was then cooled to 30° C. and isopropanol (10.00 g) was added. The stir rate was increased to 500 rpm and pyrrolidine (2.38 g) was added slowly. The reaction was then heated to 60° C. to provide the final product.

Example 4: Reaction of Maleic Anhydride, 2-Ethylhexanol, Methanol, and Various Amines The reagents used in this Example and corresponding amounts of each are listed in Table 2.

TABLE 2

Reagents for Reaction of Maleic Anhydride, 2-Ethylhexanol, Methanol, and Various Amines

| Reaction | Maleic Anhydride Weight (g) | 2-ethylhexanol Volume (mL) | Amine | Amine Volume (mL) | Methanol Volume (mL) |
|---|---|---|---|---|---|
| 9 | 1.50 | 2.40 | Pyrrolidine | 1.19 | 5.73 |
| 10 | 1.50 | 2.40 | 3-(1-pyrrolidinyl)propylamine | 2.05 | 6.78 |
| 11 | 1.50 | 2.40 | Dibutylamine | 2.47 | 6.80 |
| 12 | 1.50 | 2.40 | 3-(1-azepanyl)propylamine | 2.47 | 7.29 |
| 13 | 1.50 | 2.40 | 3-(dibutylamino)propanamine | 3.26 | 7.85 |

Generally, the procedure for each reaction was as follows. Maleic anhydride and 2-ethylhexanol were added to a 20-mL vial with a stir bar and heated to 80° C. for one hour with a 250 rpm stir rate. The reaction was cooled to 60° C. The amine was then added. After addition of the amine, the reactions became highly viscous. The temperature was increased to 80° C. for two hours. The reactions were then cooled to 50° C. and methanol was added. Vortex was required for full solvation.

Example 5: Reactions of Maleic Anhydride with Dibutylaminoethanol

The reagents used in this Example and corresponding amounts of each are listed in Table 3.

TABLE 3

Reagents for Reaction of Maleic Anhydride and Dibutylaminomethanol

| Reaction | MA wt. (g) | 2-dibutyl-amino-methanol wt. (g) | Oleylamine wt. (g) | Octylamine wt. (g) | Toluene wt. (g) | AA wt. (g) |
|---|---|---|---|---|---|---|
| 14 | 1.13 | 2.0 | 3.09 | — | 7.05 | 0.832 |
| 15 | 1.13 | 2.0 | — | 1.49 | 5.45 | 0.832 |

In a 40-mL vial, 2-dibutylaminoethanol was mixed with maleic anhydride overnight at 60° C. Oleylamine or octylamine was added and heat was increased to 70° C. After two hours, toluene was added to aid solubility. Toluene was more effective in reaction 14. In reaction 14, the solution was miscible at 80° C. After two hours, acrylic acid was added and heated at 70° C. for four hours. The product of reaction 15 was not soluble.

Example 7: Reaction of Maleic Anhydride with Hexyldecanol and DBAPA

Reaction 16:
ISOFOL 16 (hexyldecanol; 4.02 g) was charged to a vial and heated to 50° C. Maleic anhydride (1.62 g) was added with stirring. The mixture slowly dissolved. After thirty minutes, the temperature was increased to 75° C. overnight, and the mixture turned homogenous. The temperature was increased to 85° C. for 15 minutes. Then, DBAPA (3.07 g) was added. The mixture was clear. The temperature was increased to 95° C. to provide the final product.

Reaction 17:
Maleic anhydride (1.55 g) and ISOFOL 16 (3.82 g) were charged to a vial at room temperature and then heated to 85° C. for six hours. Then, the reaction was cooled to 65° C. The mixture was then added dropwise to a stirred solution of DBAPA (2.94 g) at 65° C. The mixture turned orange and became more viscous. The reaction was heated at 65° C. for 15 minutes, and then acrylic acid (1.13 g) was added. The mixture was heated overnight at 100° C. Infrared spectroscopy showed the reaction reached completion.

Reaction 18:
Maleic anhydride (2.05 g) and ISOFOL 16 (5.07 g) were charged to a vial at room temperature. The mixture was stirred and warmed to 80° C. for four hours, then to 95° C. for one hour. DBAPA (1.94 g) was then added dropwise with stirring to produce a clear tan mixture and aged overnight at 100° C. The reaction produced a clear viscous liquid.

Reaction 19:
Maleic anhydride (26.44 g) and ISOFOL 16 (65.94 g) were charged to a vial with mechanical stirring in a nitrogen atmosphere to produce a heterogeneous mixture. The mixture was heated to 85° C. for 8 hours and cooled to room temperature to provide a clear homogenous mixture. Then, DBAPA (50.03 g) was added dropwise and reacted exothermically from 25° C. to 40° C. The temperature was then increased to 70° C. for eight hours. A clear tan mixture was produced.

Overall, reactions 16-19 proceeded as depicted in Scheme 6.

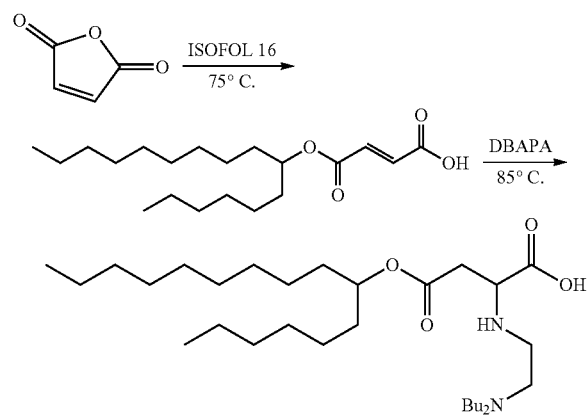

Scheme 6. Reaction of Maleic Anhydride, ISOFOL 16, and DBAPA

Example 7: Reaction of Maleic Anhydride, Ethoxylated Alcohols, and Various Amines Reaction 20:
In a vial, 2-ethyl hexanol+3EO (ECOSURF EH3) (15.10 g) and maleic anhydride (5.64 g) were charged and warmed to 80° C. for eight hours, then cooled to room temperature.

DBAPA (10.72 g) was added dropwise and reacted exothermically to 26° C. A delayed exothermic reaction to 80° C. occurred. The reaction was cooled to 75° C. before additional heat was applied. The temperature was maintained at 75° C. for six hours. The temperature was increased to 92° C. and produced some darky, oily portions. The reaction was no longer homogenous. The mixture was stirred at 50° C. and produced a homogenous tan honey-like mixture. This product (4.95 g) was charged to a vial with acrylic acid (0.66 g) and warmed to 100° C. overnight. This reaction produced a tan slick viscous oil. The reaction proceeded according to Scheme 7.

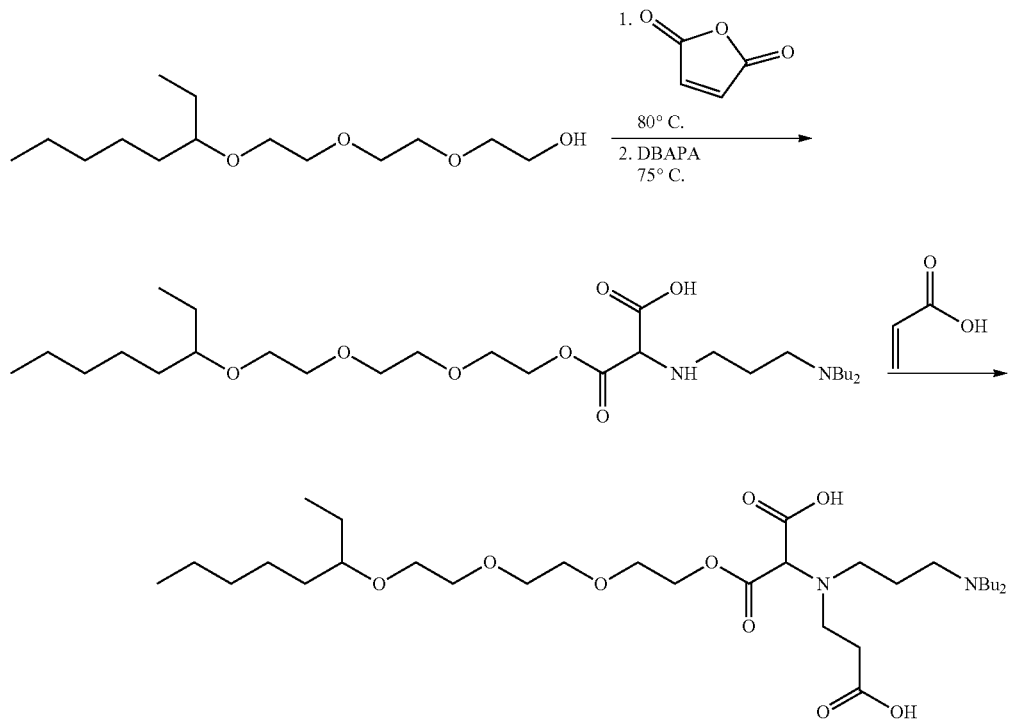

Reaction 21:

2-ethylhexanol+3EO (15.34 g) was charged to a vial with maleic anhydride (5.74 g) and warmed to 55° C., then to 60° C. DBAPA (10.98 g) was slowly added to the vial. The temperature of the reaction was held at 60° C. for six hours, and then cooled to room temperature to produce a very thick, clear glassy oil. The yield was 27.11 grams. This product (3.84 g) was charged to a vial with acrylic acid (5.16 mg) and warmed to 65° C., and then to 75° C. after fifteen minutes. The reaction was held at 75° C. overnight and cooled to room temperature to produce an orange viscous liquid.

Reaction 22:

2-ethylhexanol+3EO (ECOSURF) (14.97 g) and maleic anhydride (5.60 g) were charged to a vial and heated to 60° C. for six hours. The reaction was then cooled to room temperature. Oleylamine (15.03 g) was added to the reaction at room temperature. The reaction was warmed to 65° C. for five hours. The yield was 32.26 grams. The product (3.46 g) was then charged to a vial with acrylic acid (0.405 g) and heated to 75° C. overnight. A clear yellow oil was produced.

Reaction 23:

2-(octyloxy)ethanol and maleic anhydride were charged to a vial and heated to 60° C. for six hours. The reaction was then cooled to room temperature. DBAPA was added to the reaction and heated until the reaction was complete.

Example 8: Reaction of Maleic Anhydride with Various Dodecanol Alcohols and Various Amines Reaction 24:

To a vial, 11-methyldodecanol (13.49 g) was added to maleic anhydride (6.61 g). The mixture was warmed to 65° C. for six hours and then cooled to room temperature. The mixture was then warmed to 40° C. and DBAPA (12.54 g) was added dropwise. This reacted exothermically to 80° C. The reaction was cooled to 70° C. and aged for six hours. The mixture was then cooled to room temperature. The product (4.6 g) was then charged to a vial with acrylic acid (0.697 g) and warmed to 75° C. overnight. A glassy oil was produced. The reaction proceeded according to Scheme 8.

Scheme 8. Reaction of 11-methyldodecanol with Maleic Anhydride

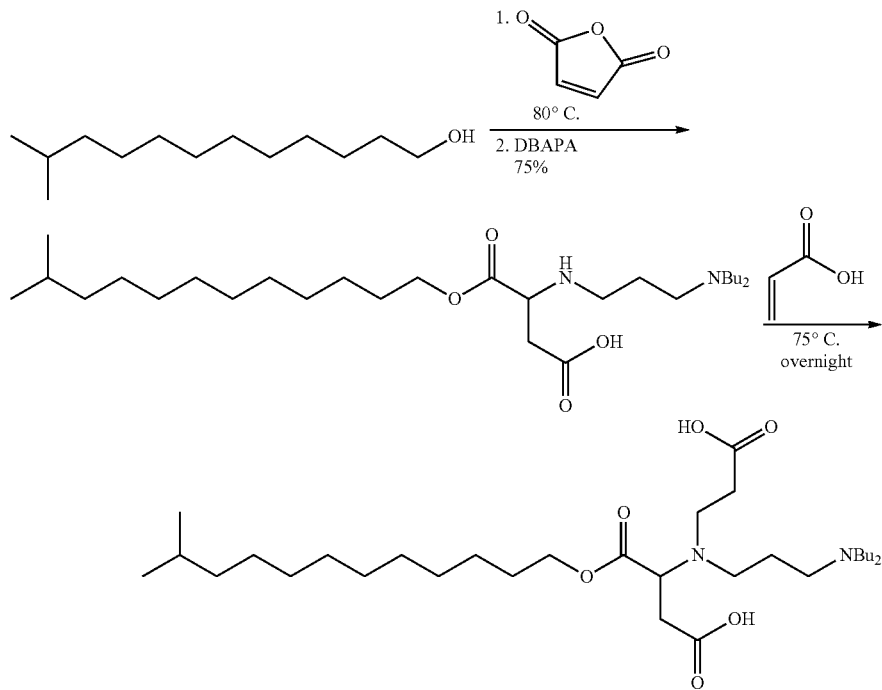

Reaction 25:

1-dodecanol (14.88 g) was charged to a vial with maleic anhydride (7.84 g). The mixture was warmed to 65° C. for six hours and then cooled to room temperature to produce a white solid. The solid was warmed to 50° C. to melt. DBAPA (14.88 g) was added dropwise and reacted exothermically to 80° C. The reaction slowly cooled to 70° C. for six hours and was finally cooled to room temperature. The product (4.72 g) was charged to a vial with acrylic acid (0.738 mg) and warmed to 75° C. overnight. A glassy oil was produced. The reaction proceeded according to Scheme 9.

Scheme 9. Reaction of 1-Dodecanol with Maleic Anhydride

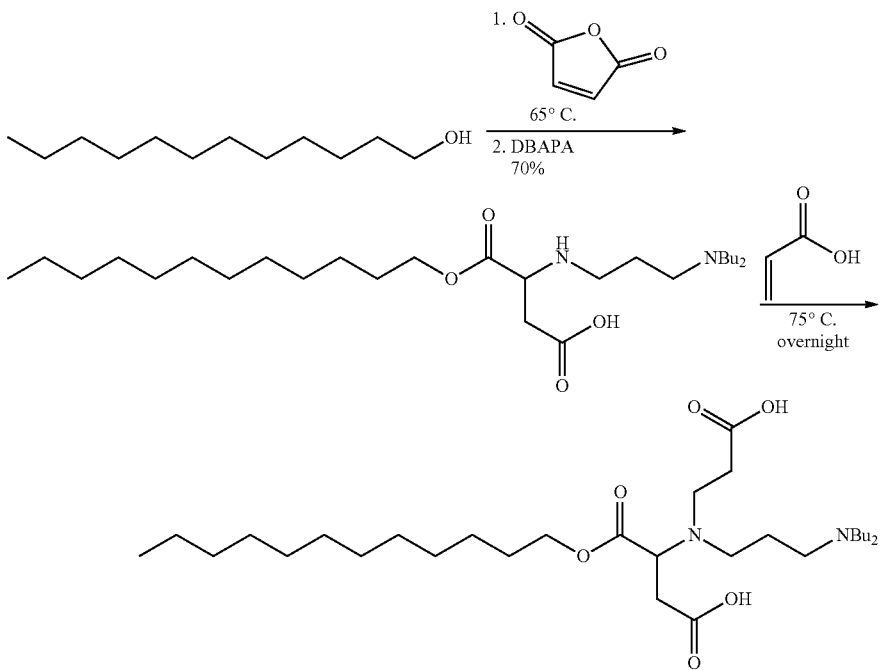

Reaction 26:

Maleic anhydride (6.89 g) was charged to a vial with 1-dodecanol (13.07 g). The mixture was warmed to 60° C. for three hours, then to 70° C. for two hours. The mixture turned opaque with white solids. The temperature was increased to 75° C. for five hours and then cooled to room temperature to produce a solid white mass. The solid was warmed to 75° C. to melt. Azepane propylamine (10.96 g) was added dropwise and reacted exothermically to a maximum of 110° C. The mixture was cooled slowly over three hours to 80° C. The reaction proceeded according to Scheme 10.

Scheme 10. Reaction of 1-Dodecanol with Maleic Anhydride and Azepane Propylamine

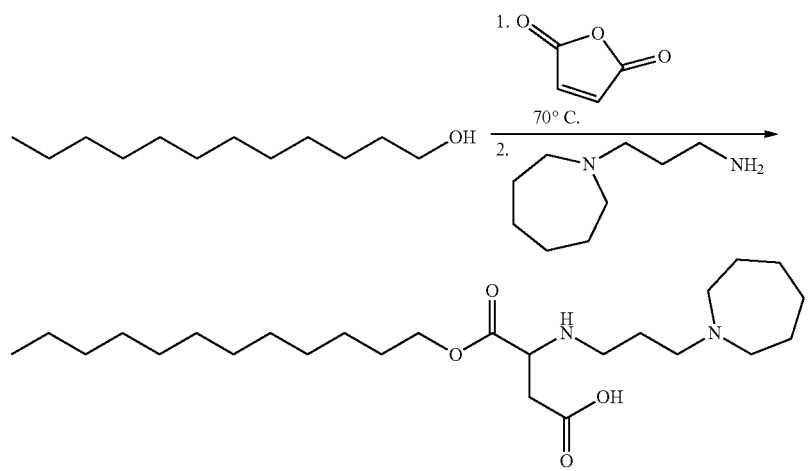

Reaction 27:

Maleic anhydride (5.77 g) was charged to a vial with 11-methyldodecanol (11.89 g) and warmed to 60° C. for three hours, then to 75° C. for eight hours. The reaction was cooled to room temperature overnight to produce a clear liquid. Then, azepane propylamine (9.18 g) was added dropwise and reacted exothermically to 65° C. The reaction was warmed to 72.5° C. for five hours and produced a tan oil. The reaction proceeded according to Scheme 11.

Scheme 11. Reaction of 11-Methyldodecanol with Maleic Anhydride and Azepane Propylamine

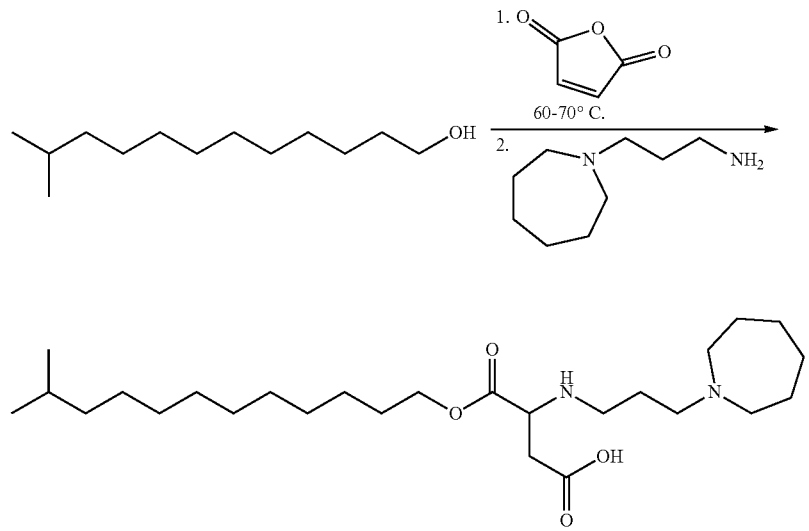

Example 9: Reaction of Maleic Anhydride with Various Oleyl Derivatives and Various Amines Reaction 28:

Maleic Anhydride (5.01) was charged to a vial with 16-methyl oleic acid+5EO (23.41 g) and warmed slowly to 60° C., where it was held for one hour to produce a clear yellow mixture. The mixture was then warmed to 75° C. for eight hours before cooling to room temperature. A clear yellow and viscous oil was produced at 23° C. Then, DBAPA (9.31 g) was added dropwise slowly and reacted very slowly exothermically to 26° C. after five minutes. The mixture was then warmed to 50° C. and the mixture began a slow exothermic reaction to 80° C. maximum. The mixture was cooled slowly to 65° C. and aged at 65° C. for six hours. The reaction proceeded according to Scheme 12.

Scheme 12. Reaction of 16-Methyl Oleic Acid + 5EO with Maleic Anhydride and DBAPA

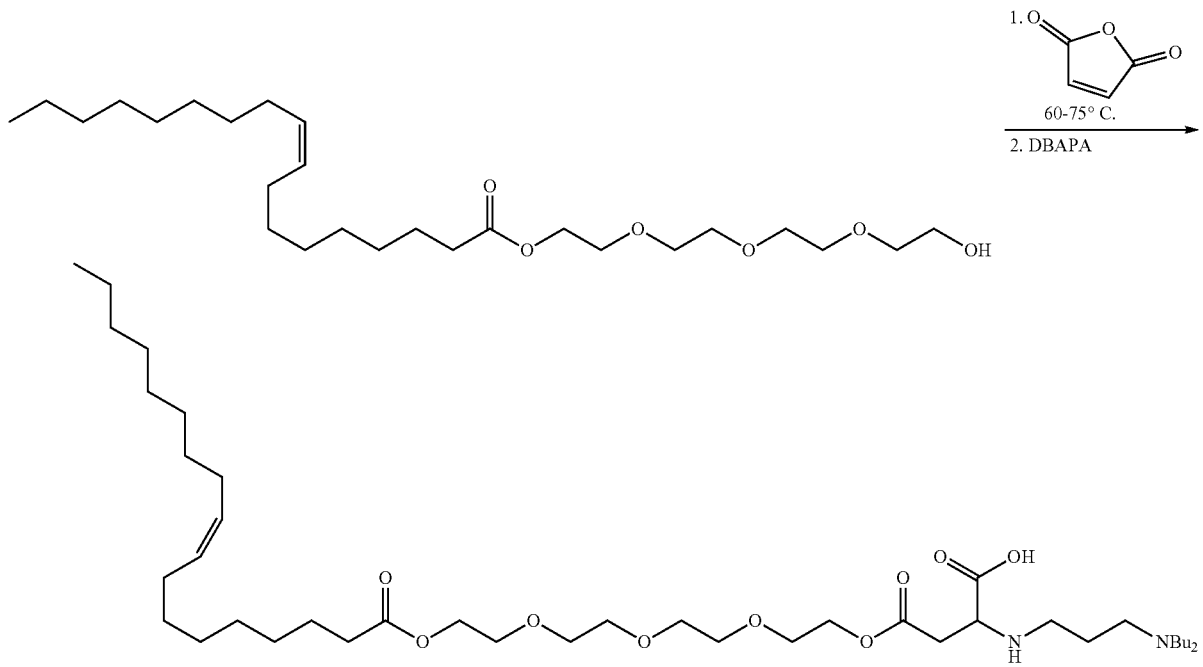

Reaction 29:

Maleic anhydride (4.31 g) was charged to a vial with oleamide+5EO (21.33 g) and warmed to 60° C. for one hour. The solids slowly dissolved. The temperature was increased to 75° C. for eight hours and then cooled to room temperature to produce a thick tan brown mixture. The mixture was warmed to 45° C. so that the stir bar was able to move. DBAPA (8.01 g) was added dropwise, which reacted exothermically to 80° C. The mixture was aged at 65° C. for six hours. The reaction proceeded according to Scheme 13.

Scheme 13. Reaction of Oleamide + 5EO with Maleic Anhydride and DBAPA

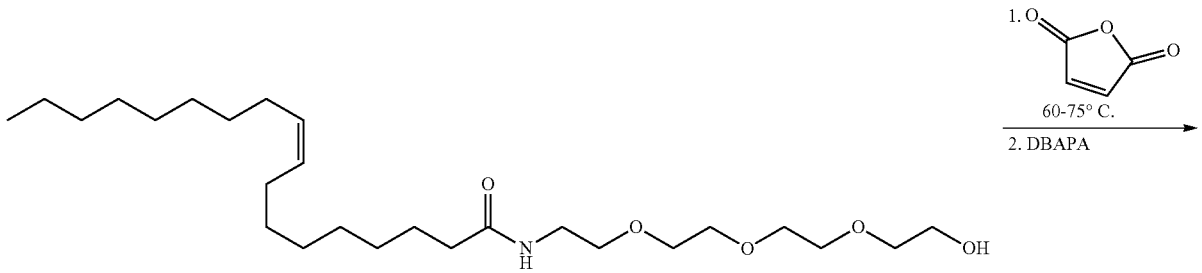

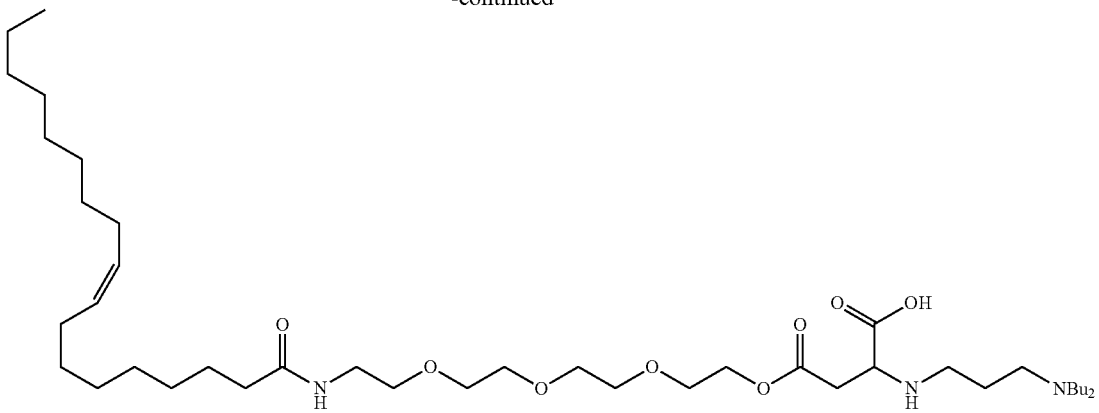

Reaction 30:

Oleic acid+12EO (43.77 g) was charged to a vial with maleic anhydride (5.29 g) and warmed to 60° C. to form a homogenous mixture, then to 75° C. for eight hours to produce a dark tan mixture. DBAPA (6.24 g) was added dropwise and did not react exothermically. The product remained a bi-phasic mixture. The temperature was increased to 50° C. and the mixture began to mix and exothermically react to 90° C. maximum. The mixture was aged at 65° C. for eight hours and was homogenous.

Reaction 31:

Oleic ester+12 EO (depicted below; 17.94 g) was charged to a vial and azepane propylamine (3.04 g) was added dropwise. There was a minimal exothermic reaction to 25° C. The mixture was bi-phasic. Temperature was increased to 50° C. and stirring was increased. The mixture began reacting exothermically as the layers became miscible to 91° C. The mixture was aged for eight hours at 65° C. to produce a homogenous mixture.

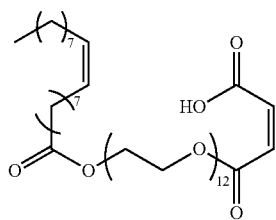

Reaction 32:

Oleyl alcohol (13.25 g) was charged to a vial with maleic anhydride (4.80 g) and produced a heterogeneous mixture. The mixture was warmed slowly to 60° C. for one hour and began clearing. The temperature was increased to 72° C. for 7 hours and produced a clear oil. DBAPA (8.99 g) was added dropwise and reacted exothermically. The reaction was heated at 60° C. for five hours and then cooled to room temperature to produce a clear, viscous oil.

Reaction 33:

Oleyl alcohol (17.04 g) was charged to a vial with maleic anhydride (6.17 g) and warmed to 60° C. for one hour. The temperature was increased to 72° C. for eight hours. Upon cooling to room temperature, a clear oil was produced. Azepane propylamine (9.62 g) was added dropwise and reacted exothermically to 70° C. The reaction was stirred at 60° C. for five hours, and then cooled to room temperature. The mixture produced a white-tan, glassy solid.

Example 10: Reaction of Maleic Anhydride with Various Alcohols and Amines

Reaction 34:

Maleic anhydride (7.51 g) was charged to a vial, followed by decanol (12.11 g), and warmed to 60° C. for two hours, then to 75° C. for six hours. The mixture was cooled to room temperature and formed a white solid. The solid was heated to 45° C. and began to melt. The temperature was increased to 50° C. and DBAPA (1.396 g) was added dropwise while the mixture reacted exothermically to a maximum temperature of 90° C. The reaction was cooled to 65° C. and aged for six hours to produce a tan viscous oil. The product (4.19 g) was charged to a vial with acrylic acid (0.696 g) and warmed to 85° C. overnight to produce a viscous oil.

Reaction 35:

Maleic anhydride (8.20 g) and octanol (10.80 g) were charged to a vial and warmed to 60° C. for one hour. The temperature was increased to 75° C. for six hours and then cooled at room temperature overnight to form a white solid. The solid was warmed to 45° C. and began to melt. DBAPA (15.25 g) was added dropwise and the mixture reacted exothermically to a maximum temperature of 90° C. The reaction was slowly cooled to 65° C. for six hours to produce a tan viscous oil. The product (3.40 g) was charged to a vial with acrylic acid (0.603 g) and the mixture was warmed to 85° C. overnight to produce a viscous oil.

Reaction 36:

Octanol+6EO (39.38 g) was charged to a vial with maleic anhydride (9.7 g). The heterogeneous mixture was warmed to 72° C. for eight hours and gradually became homogenous. The mixture was cooled to room temperature. At 22° C., the mixture was clear. DBAPA (18.02 g) was added dropwise and reacted exothermically to 60° C. by the end of the addition. The reaction was maintained at 60° C. for five hours and then cooled to room temperature to produce a clear yellow, viscous oil.

Reaction 37:

Tridecanol+8EO (37.10 g) was charged to a vial with maleic anhydride (6.04 g) and warmed to 60° C. for two hours to produce a clear yellow-tan mixture with some crystal growth on the sides of the vial. The mixture was warmed to 70° C., then to 75° C. overnight to produce a clear liquid. When the mixture was cooled to 35° C., the mixture remained liquid. DBAPA (11.18 g) was added dropwise with vigorous stirring and reacted exothermically to 55° C. The temperature was increased to 60° C. for five hours.

Reaction 38:

Maleic anhydride (6.91 g) and 2-butyloctanol (13.11 g) were added to a vial, and the mixture was heated to 80° C. for 6-8 hours. Then, DBAPA (13.10 g) was added to yield 25.97 grams of the final product.

Reaction 39:

Tetrahydrofurfural alcohol (10.02 g) was added to a vial with maleic anhydride (9.67 g). The temperature cooled to 11.2° C. upon addition of the maleic anhydride. The mixture was heated to 80° C. for 6-8 hours. Oleyl amine (26.203 g) was added to the mixture dropwise and heated at 80° C. The yield of the final product was 38.118 grams.

Reaction 40:

Isostearyl alcohol (14.835 g) was added to a vial with maleic anhydride (5.160 g). The mixture was heated to 80° C. for 2-3 hours. DBAPA (9.794 g) was added to the mixture to provide the final product in a yield of 23.385 grams.

Reaction 41:

Maleic anhydride (4.344 g) was added to a vial with 2-decyltetradecanol (15.671 g). The mixture was heated to 80° C. for several hours. Then, DBAPA (8.233 g) was added to provide the final product in a yield of 24.962 grams.

Reaction 42:

Maleic anhydride (7.651 g) was added to a vial with 1-decanol (12.345 g). The mixture was heated at 60° C. for four hours. Then, piperidine propylamine (10.00 g) was added and the reaction was heated at 80° C. for eight hours to provide the final product.

Reaction 43:

Maleic anhydride (7.661 g) was added to a vial with 1-decanol (12.355 g). The mixture was heated at 50° C. with stirring for five hours. DBAPA (12.170 g) was slowly added and the reaction was heated at an elevated temperature for several hours to provide the final product.

Example 11: Rocking Cell Tests

A Sapphire Rocking Cell RCS is commercially available from PSL Systemtechnik in Germany. The Sapphire Rocking Cell is a laboratory instrument used to test the performance of low dosage hydrate inhibitors. The compounds were evaluated based on their ability to effectively minimize the size of gas hydrate agglomerate particles and disperse those particles into the hydrocarbon phase. Chemical performance was evaluated by determining the maximum treatable water cut (water to oil ratio) and the minimum chemical dosage to register a pass in the rocking cell test.

A rocking cell has two parts, a manifold and a cell body. The manifold is made up of stainless steel fittings that are welded together. It has three stems. An inlet stem is used to charge gas into the cell. An outlet stem is used to release the gas out of the cell. The third stem connects to a transducer, which measures the pressure inside of the cell. The cell body has three layers. The outer layer is a polycarbonate tube, which has a thickness of 0.7 cm. The middle layer is made of stainless steel metal and is connected to the manifold. The inner layer is a high-pressure sapphire tube, which has an outer diameter of 2.8 cm, inner diameter of 1.85 cm, and length of 5 cm. This sapphire tube can handle up to 3000 psi. A stainless steel ball which has a diameter of 1.6 cm is located inside the sapphire tube to induce turbulence and mix fluids during the rocking process.

Test fluids usually contain three components. For the anti-agglomerate test, 7.2 mL of warm crude oil was first injected into the cell. Next, a solution of 30,000 total dissolved solids (TDS) (7% by weight) of NaCl synthetic brine was injected into the cell to make a 40% water cut mixture. The anti-agglomerate test compound was the final component injected into the cell. The dosage of the test compound was based on the volume of aqueous phase. The initial temperature was set to 21° C. Observations were made every two to three hours, before the rocking was stopped, and also immediately after the restart.

Each cell was charged with Green Canyon gas and pressurized up to 2500 psi. All cells rocked for at least 1.5 to 2 hours until fluid was saturated and pressure stabilized. The rocking was ceased and the tank temperature was reduced to the set point of 4° C. over approximately 8 hours. The cells were then reboosted to a pressure of 2500 psi and remained static for 24 hours. Rocking was restarted for 2 hours with frequent observations to rank each cell with a ranked set of pass/fail criterion. Pressure and tank temperature data was recorded during this time.

The pass/fail criteria are based on the ability of the ball in the rocking cell to move within the sapphire tube. For example, the anti-agglomerant passes the rocking cell test if at the time of the ranking, the ball moves freely when the cell is rocked indicating that few agglomerates have formed. In contrast, the anti-agglomerant fails if the ball's movement is obstructed or completely stopped by the formation of gas hydrate agglomerates. The anti-agglomerate's performance is borderline when there are observable gas hydrate agglomerates and at least some of the agglomerates are stuck to the walls of the sapphire tube; when these agglomerates are present and the movement of the ball is not restricted, the anti-agglomerant ranking is a borderline pass.

The following table shows the minimum effective dose in order to provide a test with a pass ranking.

| Example | Oil A (55% w/c) | Oil B (25% w/c) | Oil C (35% w/c) | Oil D (25% w/c) |
|---|---|---|---|---|
| | Minimum Effective Dose (MED) (vol. %) | | | |
| Reaction 19 | 3.0 | 3.0 | 3.0 | 3.0 |
| Reaction 21 | 3.5 | — | 3.0 | 1.0 |
| Reaction 24 | — | 2.0 | 3.0 | 2.0 |
| Reaction 26 | — | 2.0 | >3.0 | 2.0 |

For the product of Reaction 23, testing in an oil-containing fluid having 30% water cut, 0.75 volume percent provided a pass ranking and in an oil-containing fluid having a 60% water cut, 1.25 volume percent provided a pass ranking.

Example 12: Biodegradation Test

The biodegradation test was performed using the OECD 306 (Biodegradability in Seawater).

| Study number | ThOD (mgO$_2$/mg) | Addition rate (mg/l) | Day 7 (%) | Day 14 (%) | Day 21 (%) | Day 28 (%) |
|---|---|---|---|---|---|---|
| 9 | 2.437 | 2.134 | 25 | 32 | 34 | 28 |
| Reference | 1.66 | 2.0 | 69 | 68 | 68 | 67 |

Example 13: Toxicity Tests

The toxicity tests were of a semi static design. For the limit, range-finding, and definitive tests one replicate was set up for each test concentration along with one control vessel. The duration of the tests are indicated in the tables. The maximum loading was 1.0 g fish/litre, there was 12-16 hours of light per day, the temperature was 20° C.±2° C., the pH was from 6-9, and the salinity was 36±4%. Dissolved oxygen, pH, temperature and salinity were measured at 0 hours, 24 hours, 48 hours, 72 hours, and 96 hours (where the testing was that duration).

First stage limit test. A limit test was conducted using the EC50 from the algae test. Ten test animals were exposed at the limit concentration. If no significant mortality occurred in the fish test, the experimental phase of the study was considered complete. If significant mortality occurred during a limit test, the test was terminated immediately and the fish were euthanized. Significant mortality was defined as >10% mortality in a test vessel.

Second stage limit test. If significant mortality occurs in the first stage limit test, a further limit test was conducted using a concentration lower than the first limit test. If no significant mortality occurs in this test, the experimental phase of the study was considered complete.

Full toxicity test. If significant mortality occurs in the second stage limit test, a full toxicity test was conducted to establish an LC50 value. The range-finding test to provide the range-finding result below was conducted at the concentrations derived from the limit tests. At least four test concentrations were used in a geometric series with a maximum factor of 10. Five test animals were exposed per test concentration. A definitive test to provide the definitive result below was conducted at concentrations derived from the range-finding tests. Ten test animals were exposed per test concentration. At least five test concentrations were used in a geometric series with a maximum factor of 3.2. The results of the compound prepared in Reaction 23 for these tests are below.

| Study Number | Test | Range-finding result (mg/l) | Definitive result (mg/l) |
|---|---|---|---|
| 3 | 72 hr Algae *Skeletonema* sp. EC$_{50}$ test | 26.62 | 18 |

| Study Number | Test | Range-finding result (mg/l) | Definitive result (mg/l) |
|---|---|---|---|
| 1 | 48 hr Crustacean *Acartia tonsa* LC$_{50}$ test | 30.1 | 31.2 |

| Study Number | CAS number | Percentage composition | Theoretical log P$_{ow}$ value |
|---|---|---|---|
| 19 | Proprietary | 60-100% | 1.80* |

| Study Number | Test | Test result (mg/kg) |
|---|---|---|
| 2 | 10 day *Corophium volutator* LC$_{50}$ test | 7,361 |

| Study Number | Test | Test result (mg/kg) |
|---|---|---|
| 22 | 96 hr Juvenile fish *Cyprinodon variegatus* limit test | No effect at 18 |

These test results show acceptable toxicity results and that a concentration of greater than 10 ppm is tolerated by tested marine species.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compounds, compositions and methods without departing from the scope of the invention, it is intended that all matter contained in the above description shall be interpreted as illustrative and not in a limiting sense.

The invention claimed is:

1. A compound having the structure of formula (Ia) or an acid, a free base, a zwitterion, or a salt thereof:

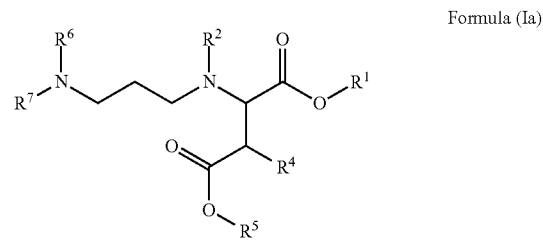

Formula (Ia)

wherein
$R^1$ is $C_{10}$ to $C_{24}$ alkyl or alkenyl or straight or branched $C_6$-$C_{24}$ alkyl and contains 1 to 12 ethylene oxide units;
$R^5$ is hydrogen;
$R^2$ is hydrogen;
$R^4$ is hydrogen; and
$R^6$ and $R^7$ are independently alkyl or $R^6$ and $R^7$ together with the nitrogen they are attached to form a ring.

2. The compound of claim 1, wherein $R^6$ and $R^7$ are the same.

3. A compound having the structure of formula (Ie) or an acid, a free base, a zwitterion, or a salt thereof:

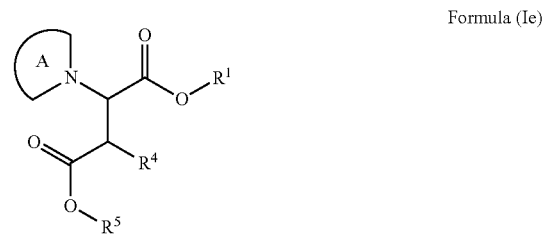

Formula (Ie)

wherein
R¹ is hydrogen;
(ii) R⁵ is $C_{10}$ to $C_{24}$ alkyl or alkenyl or straight or branched $C_6$-$C_{24}$ alkyl and contains 1 to 12 ethylene oxide units;
R⁴ is hydrogen;
A is a nitrogen-containing heterocycle, wherein the nitrogen-containing heterocycle is an optionally substituted pyrrolidine, piperidine, pyrazolidine, imidazolidine, isoxazolidine, oxazolidine, or azepane.

4. The compound of claim 3, wherein the nitrogen-containing heterocycle is pyrrolidine, piperidine, pyrazolidine, imidazolidine, isoxazolidine, oxazolidine, or azepane.

5. A compound selected from the group consisting of:

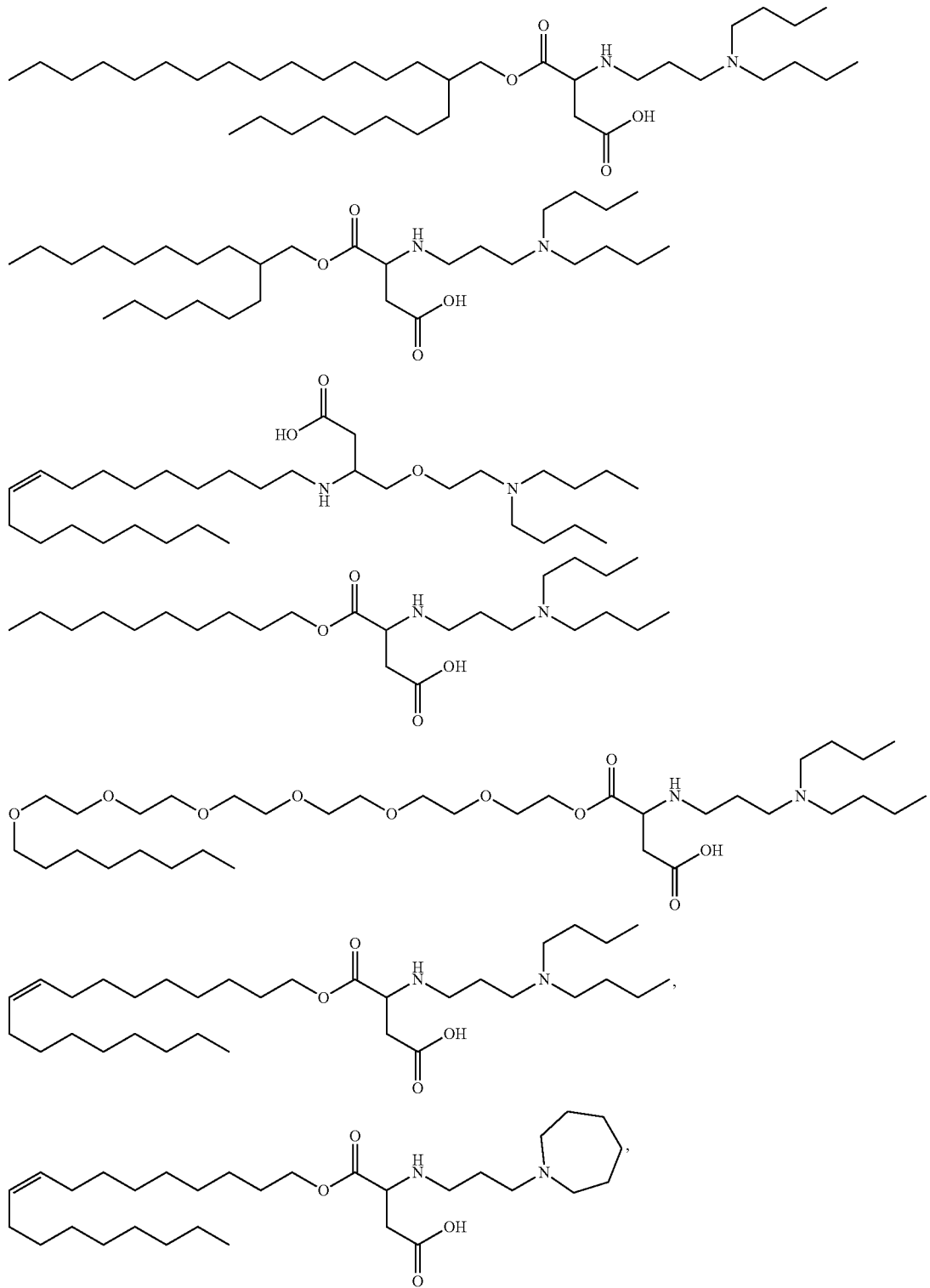

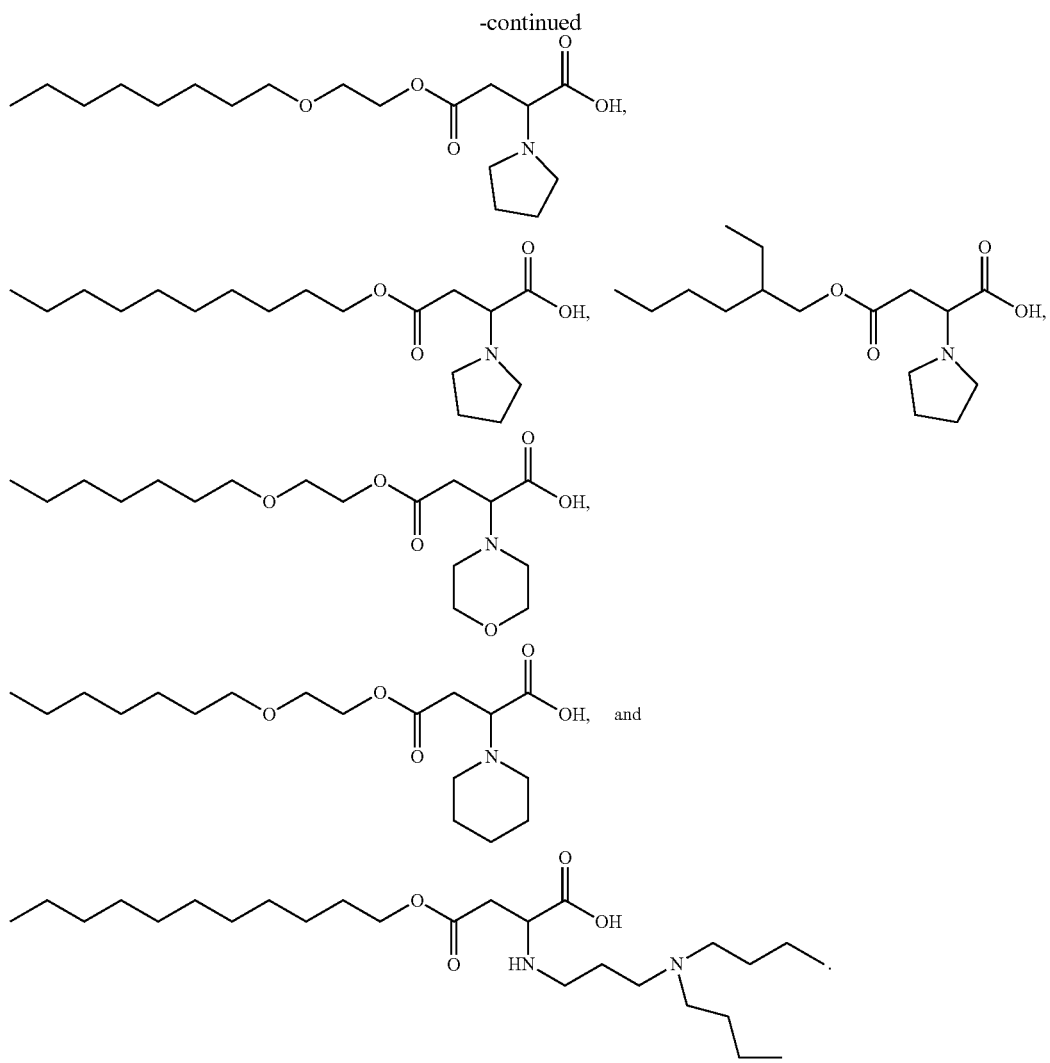

6. A hydrate inhibitor composition comprising a hydrate-inhibiting effective amount of a compound of formula (I) of claim 1.

7. A method of inhibiting formation of hydrate agglomerants in a fluid comprising water, a gas, and optionally a liquid hydrocarbon, the method comprising contacting the fluid with an effective amount of a hydrate inhibitor composition of claim 6.

8. The compound of claim 1, wherein $R^1$ is $C_{10}$ to $C_{24}$ alkyl.

9. The compound of claim 1, wherein $R^1$ is $C_{10}$ to $C_{24}$ alkenyl.

10. The compound of claim 1, wherein $R^1$ is straight or branched $C_6$-$C_{24}$ alkyl and contains 1 to 12 ethylene oxide units.

11. The compound of claim 1, wherein $R^6$ and $R^7$ are independently alkyl.

12. The compound of claim 1, wherein $R^6$ and $R^7$ are independently $C_1$ to $C_6$ alkyl.

13. The compound of claim 5, comprising:

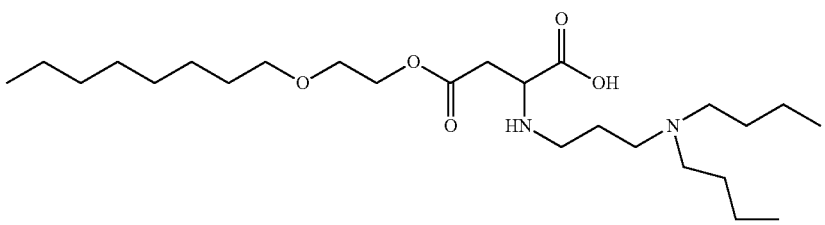 [SMILES: CCCCCCCCOCCOC(=O)CC(NCCCN(CCCC)CCCC)C(=O)O]

14. The compound of claim 3, wherein A is pyrrolidine.

15. The compound of claim 14, wherein $R^5$ is $C_{10}$ to $C_{24}$ alkyl or alkenyl.

16. The compound of claim 14, wherein $R^5$ is straight or branched $C_6$-$C_{24}$ alkyl and contains 1 to 12 ethylene oxide units.

\* \* \* \* \*